United States Patent
Mita et al.

[11] Patent Number: 5,969,138
[45] Date of Patent: Oct. 19, 1999

[54] PYRROLIDINONE DERIVATIVES

[75] Inventors: Naruyoshi Mita; Hiroshi Nagase; Hajime Iizuka, all of Chiba; Takahisa Oguchi, Ibaraki; Kazuya Sakai, Chiba; Kazutoshi Horikomi, Chiba; Takaichi Miwa, Chiba; Shinji Takahashi, Chiba, all of Japan

[73] Assignee: Mitsui Chemicals, Inc., Tokyo, Japan

[21] Appl. No.: 08/961,221

[22] Filed: Oct. 30, 1997

[30] Foreign Application Priority Data

Nov. 1, 1996 [JP] Japan .................................. 8-291587

[51] Int. Cl.⁶ .................................................. C07D 241/02
[52] U.S. Cl. .......................... 544/407; 544/372; 514/252
[58] Field of Search .............................. 544/372; 514/252

[56] References Cited

U.S. PATENT DOCUMENTS

| | | | |
|---|---|---|---|
| 4,547,504 | 10/1985 | Fabre et al. | 514/255 |
| 4,767,759 | 8/1988 | Weber et al. | 514/235.5 |
| 5,538,985 | 7/1996 | Iizuka et al. | 514/326 |

FOREIGN PATENT DOCUMENTS

| | | |
|---|---|---|
| 7-252219 | 10/1995 | Japan . |
| 9-40667 | 2/1997 | Japan . |

OTHER PUBLICATIONS

Patent Abstracts of Japan, vol. 096, No. 002, Feb. 29, 1996 & JP 07252219A (Mitsui Toatsu Chemicals, Inc.), Oct. 3, 1985, *Abstract*.

Burt et al, *Proc. Nat. Acad. Sci USA*, "Dopamine Receptor Binding in the Corpus Striatum of Mammalian Brain", vol. 72, No. 11, pp. 4655–4659, 1975.

Vilner et al, *Multiple Sigma and PCP Receptor Ligands: Mechanisms for Neuromodulation and Neuroprotection?*, Characterization of Sigma–Like Binding Sites of NB41A3, S–20Y, and N1E–115 Neuroblastomas, C6 Glioma, and NG108–15 Neuroblastoma–Glioma Hybrid Cells: Further Evidence for Sigma–2 Receptors, pp. 341–353, 1992.

*Primary Examiner*—Emily Bernhardt
*Attorney, Agent, or Firm*—Burns, Doane, Swecker & Mathis, L.L.P.

[57] ABSTRACT

Since a compound represented by general formula (1), its pharmaceutically acceptable salt and a hydrate of the pharmaceutically acceptable salt have high antipsychotic activity, they may be used as an active ingredient for preparation of an antipsychotic.

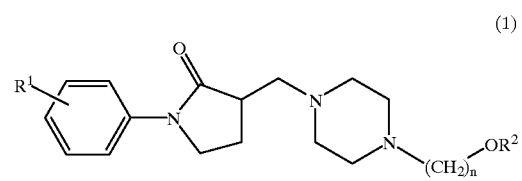

(1)

Also provided are an optical resolution method of the above compound and an intermediate for preparation of the compound.

15 Claims, No Drawings

PYRROLIDINONE DERIVATIVES

FIELD OF THE INVENTION

This invention relates to novel pyrrolidinone derivatives. In particular, this invention relates to a compound represented by formula (1) useful for treatment of disorders including central nervous systems disorders such as schizophrenia, dementia, manic-depressive psychosis, anxiety, drug poisoning and ischemic brain diseases; disorders associated with immunopathy or endocrine disturbance; and digestive system ulcers; to its pharmaceutically acceptable salt; to a hydrate of the pharmaceutically acceptable salt; to an optical resolution method for preparation thereof; as well as an intermediate for preparation thereof.

This invention also relates to therapeutic and/or prophylactic agents for the above disorders, comprising, as an active ingredient, a compound represented by general formula (1), a pharmaceutically acceptable salt thereof or a hydrate of the pharmaceutically acceptable salt.

DESCRIPTION OF THE RELATED ART

Central nervous systems disorders such as schizophrenia, dementia, manic-depressive psychosis, anxiety, drug poisoning and death of nerve cells due to cerebral ischemia have become significant problems in the modern society. It has been particularly desired to establish a method for treatment, improvement or prevention of the disorders.

Schizophrenia occurs at the incidence of one in 130, mostly occurring in adolescence. If remaining untreated, it will gradually impair a personality, destroying human self-development functions, which makes it a significant problem in a society. Abnormal dopamine-transmission has been implied as a contributor to schizophrenia, which maybe confirmed by the fact that dopamine antagonists such as chlorpromazine and haloperidol are effective as an antipsychotic.

Dopamine antagonists, however, have a major problem in their use that besides antipsychotic activity, they may frequently induce extrapyramidal side-effects such as acute dystonia and Parkinsonism, in particular tardive dyskinesia.

To overcome the problem, some approaches have been recently investigated from an aspect different from the conventional mechanism of action; for example sigma receptor antagonists. Since it has been shown that SKF-10047, a sigma receptor agonist, may induce psychosis-like symptoms to a human, an antagonist to the agonist may be expected to exhibit antipsychotic effect. Furthermore, if it does not have affinity for a dopamine receptor, the antagonist may be expected to be an antipsychotic without extrapyramidal side effects.

A sigma receptor antagonist may be also expected to have therapeutic effect to gastrointestinal disorders, immunological disorders or asthma, as well as central nervous systems disorders such as schizophrenia, dementia, manic-depressive psychosis, anxiety, drug poisoning and death of nerve cells due to cerebral ischemia.

U.S. Pat. No. 4,767,759 has described that a compound represented by general formula (I) has antidementia activity;

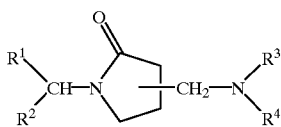

(1)

wherein $R^1$ is hydrogen or methyl; $R^2$ is phenyl or pyridyl mono- or disubstituted by a $C_{1-2}$ alkoxy, fluorine, chlorine, bromine, trifluoromethyl or a $C_{1-4}$ alkyl; $R^3$ and $R^4$, which may be the same or different, are hydrogen or a $C_{1-2}$ alkyl, or $R^3$ and $R^4$, in combination with a nitrogen atom, form a saturated 5 or 6 membered ring which may comprise O and/or N atoms as additional heteroatoms, and may be also substituted by methyl group, or form an imidazole ring having an aminoalkyl group at 4- or 5-position. It, however, has not described a sigma receptor or antipsychotic effect.

In JP-A 7-252219 there is disclosed a compound represented by general formula (II):

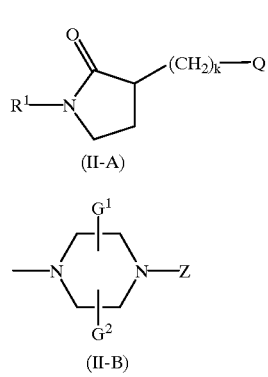

wherein in formula (II-A) $R^1$ is a $C_{1-12}$ alkyl, substituted or unsubstituted phenyl, or a substituted or unsubstituted phenylalkyl; k is an integer of 1 or 2; Q has a structure of formula (II-B) wherein $G^1$ and $G^2$ are hydrogen or a lower alkyl; Z is hydrogen, a $C_{1-18}$ alkyl, a substituted acyl, a substituted carbamoyl, phenyl, a substituted phenyl, a phenylalkyl, a substituted phenylalkyl or a substituted heterocyclic group.

There is also disclosed in JP-A9-40667, a compound represented by general formula (III):

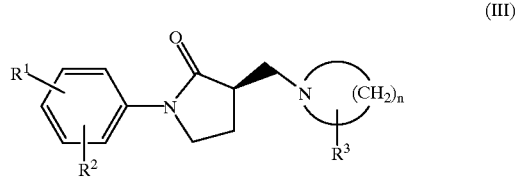

(III)

wherein $R^1$ and $R^2$ are independently hydrogen, a halogen, a $C_{1-6}$ alkyl, a $C_{1-6}$ alkoxy, a $C_{1-3}$ perfluoroalkyl or a $C_{1-3}$ perfluoroalkoxy; $R^3$ is hydrogen, hydroxy, a $C_{1-6}$ alkyl, a $C_{1-6}$ alkoxy, a $C_{1-3}$ perfluoroalkyl, a $C_{1-3}$ perfluoroalkoxy, a $C_{2-5}$ alkenyloxy or a $C_{3-5}$ alkyloxy; and n is an integer of 4 to 7.

Rimcazole is known as a sigma receptor antagonist, but has inadequate affinity or specificity to a sigma receptor.

SUMMARY OF THE INVENTION

For solving the above problems, we have intensely attempted to obtain a compound useful as an antipsychotic, and have finally found that a pyrrolidinone derivative having a particular structure, its pharmaceutically acceptable salt and a hydrate of the salt have excellent characteristics as an antipsychotic, to complete this invention.

Some aspects of this invention include;

[1] a pyrrolidinone derivative represented by general formula (1), its pharmaceutically acceptable salt and a hydrate of the pharmaceutically acceptable salt:

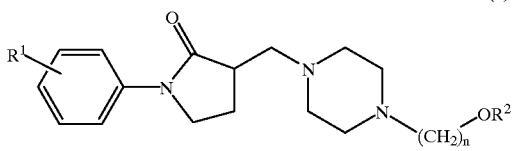

(1)

wherein $R^1$ is hydrogen or a halogen; $R^2$ is hydrogen, a $C_{1-3}$ alkyl, a $C_{2-3}$ alkenyl or a $C_{2-3}$ alkynyl; and n is an integer of 2 to 3;

[2] a pyrrolidinone derivative according to the above [1], represented by general formula (1) wherein $R^1$ is chlorine or bromine, $R^2$ is a $C_{1-3}$ alkyl, and n is 2; its pharmaceutically acceptable salt and a hydrate of the pharmaceutically acceptable salt;

[3] a pyrrolidinone derivative according to the above [1], represented by general formula (1) wherein $R^1$ is chlorine, $R^2$ is methyl, and n is 2; its pharmaceutically acceptable salt and a hydrate of the pharmaceutically acceptable salt;

[4] an optically active pyrrolidinone derivative according to the above [1], represented by general formula (2), its pharmaceutically acceptable salt and a hydrate of the pharmaceutically acceptable salt:

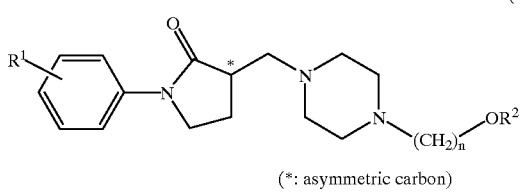

(2)

(*: asymmetric carbon)

wherein $R^1$ is hydrogen or a halogen; $R^2$ is hydrogen, a $C_{1-3}$ alkyl, a $C_{2-3}$ alkenyl or a $C_{2-3}$ alkynyl; and n is an integer of 2 to 3;

[5] an optically active pyrrolidinone derivative according to the above [4], represented by general formula (2) wherein $R^1$ is chlorine, $R^2$ is methyl, and n is 2; its pharmaceutically acceptable salt and a hydrate of the pharmaceutically acceptable salt:

[6] a dihydrate of the salt of the optically active pyrrolidinone derivative according to the above [4], represented by general formula (2) wherein $R^1$ is chlorine, $R^2$ is methyl, and n is 2.

An optical resolution method of this invention comprises;
preparing a mixture of diastereomer salts from a racemic modification of a pyrrolidinone derivative represented by formula (1) wherein $R^1$ is hydrogen or a halogen, $R^2$ is hydrogen, a $C_{1-3}$ alkyl, a $C_{2-3}$ alkenyl or a $C_{2-3}$ alkynyl, and n is an integer of 2 to 3, and optically active mandelic acid or optically active tartaric acid;
separating the diastereomer salt of the optically active pyrrolidinone derivative of the above [4] from the mixture of the diastereomer salts;
forming and collecting the optically active pyrrolidinone derivative of the above [4] from the separated diastereomer salt.

Another aspect of this invention is a salt for preparing the compound of the above [4] consisting of the optically active pyrrolidinone derivative of the above [4] represented by general formula (2), wherein $R^1$ is chlorine, $R^2$ is methyl and n is 2, and optically active mandelic acid or optically active tartaric acid.

An antipsychotic may be obtained, using any of the compounds of the above [1] to [6] as an active ingredient.

The pyrrolidinone derivative represented by general formula (1), its pharmaceutically acceptable salt and a hydrate of the pharmaceutically acceptable salt are useful for treatment of disorders including central nervous systems disorders such as schizophrenia, dementia, manic-depressive psychosis, anxiety, drug poisoning and ischemic brain disorders; disorders associated with immunopathy or endocrine disturbance; and digestive system ulcers.

This invention also provide an optical resolution method and an intermediate for preparing the pyrrolidinone derivative of this invention represented by general formula (2).

DETAILED DESCRIPTION OF THE INVENTION AND PREFERRED EMBODIMENTS

The compound of this invention will be described in detail.

Halogen in terms of $R^1$ in general formula (1) includes fluorine, chlorine, bromine and iodine, preferably chlorine and bromine, more preferably chlorine. $R^1$ may substitute preferably at the para or meta position.

A $C_{1-3}$ alkyl in terms of $R^2$ includes methyl, ethyl, n-propyl and isopropyl, preferably methyl and ethyl, more preferably methyl.

A $C_{2-3}$ alkenyl in terms of $R^2$ includes vinyl, allyl, 1-propenyl and isopropenyl.

A $C_{2-3}$ alkynyl in terms of $R^2$ includes ethynyl, 1-propynyl and 2-propynyl.

Then, n may be an integer of 2 or 3, preferably 2.

Water as a component of the hydrates may be present in the hydrates in various forms including water of crystallization and adhesive moistures. Different forms of water may be included in a single hydrate. For example, a hydrate may include either water of crystallization or adhesive moisture, or both. The hydration degree may range from 0.001 to 10, preferably, from 0.001 to 4, more preferably from 0.001 to 3. The hydration degree is not restricted to integers.

The compounds of this invention are shown in Tables 1 to 3, but this invention is, of course, not limited to these specific compounds. Each compound in the tables can be formed as (R)- or (S)-isomer, or a mixture of these isomers, i.e., racemic modification. In Table 2, Compound Nos. 1–24, 49–72, 97–120 and 145–168 are anhydrides and Compound Nos. 25–48, 73–96, 121–144 and 169–192 are dihydrates.

TABLE 1

Structure: R¹-substituted phenyl-N-pyrrolidinone-CH₂-piperazine-N-(CH₂)ₙ-OR²

| Compound No. | R¹ | R² | n |
|---|---|---|---|
| 1 | H | H | 2 |
| 2 | H | CH₃ | 2 |
| 3 | H | CH₂CH₃ | 2 |
| 4 | H | CH₂CH₂CH₃ | 2 |
| 5 | H | CH(CH₃)₂ | 2 |
| 6 | H | vinyl | 2 |
| 7 | H | allyl | 2 |
| 8 | H | 1-propenyl | 2 |
| 9 | H | isopropenyl | 2 |
| 10 | H | ethynyl | 2 |
| 11 | H | 1-propynyl | 2 |
| 12 | H | 2-propynyl | 2 |
| 13 | H | H | 3 |
| 14 | H | CH₃ | 3 |
| 15 | H | CH₂CH₃ | 3 |
| 16 | H | CH₂CH₂CH₃ | 3 |
| 17 | H | CH(CH₃)₂ | 3 |
| 18 | H | vinyl | 3 |
| 19 | H | allyl | 3 |
| 20 | H | 1-propenyl | 3 |
| 21 | H | isopropenyl | 3 |
| 22 | H | ethynyl | 3 |
| 23 | H | 1-propynyl | 3 |
| 24 | H | 2-propynyl | 3 |
| 25 | 2-F | H | 2 |
| 26 | 2-F | CH₃ | 2 |
| 27 | 2-F | CH₂CH₃ | 2 |
| 28 | 2-F | CH₂CH₂CH₃ | 2 |
| 29 | 2-F | CH(CH₃)₂ | 2 |
| 30 | 2-F | vinyl | 2 |
| 31 | 2-F | allyl | 2 |
| 32 | 2-F | 1-propenyl | 2 |
| 33 | 2-F | isopropenyl | 2 |
| 34 | 2-F | ethynyl | 2 |
| 35 | 2-F | 1-propynyl | 2 |
| 36 | 2-F | 2-propynyl | 2 |
| 37 | 2-F | H | 3 |
| 38 | 2-F | CH₃ | 3 |
| 39 | 2-F | CH₂CH₃ | 3 |
| 40 | 2-F | CH₂CH₂CH₃ | 3 |
| 41 | 2-F | CH(CH₃)₂ | 3 |
| 42 | 2-F | vinyl | 3 |
| 43 | 2-F | allyl | 3 |
| 44 | 2-F | 1-propenyl | 3 |
| 45 | 2-F | isopropenyl | 3 |
| 46 | 2-F | ethynyl | 3 |
| 47 | 2-F | 1-propynyl | 3 |
| 48 | 2-F | 2-propynyl | 3 |
| 49 | 3-F | H | 2 |
| 50 | 3-F | CH₃ | 2 |
| 51 | 3-F | CH₂CH₃ | 2 |
| 52 | 3-F | CH₂CH₂CH₃ | 2 |
| 53 | 3-F | CH(CH₃)₂ | 2 |
| 54 | 3-F | vinyl | 2 |
| 55 | 3-F | allyl | 2 |
| 56 | 3-F | 1-propenyl | 2 |
| 57 | 3-F | isopropenyl | 2 |
| 58 | 3-F | ethynyl | 2 |
| 59 | 3-F | 1-propynyl | 2 |
| 60 | 3-F | 2-propynyl | 2 |
| 61 | 3-F | H | 3 |
| 62 | 3-F | CH₃ | 3 |
| 63 | 3-F | CH₂CH₃ | 3 |
| 64 | 3-F | CH₂CH₂CH₃ | 3 |
| 65 | 3-F | CH(CH₃)₂ | 3 |
| 66 | 3-F | vinyl | 3 |
| 67 | 3-F | allyl | 3 |
| 68 | 3-F | 1-propenyl | 3 |
| 69 | 3-F | isopropenyl | 3 |
| 70 | 3-F | ethynyl | 3 |
| 71 | 3-F | 1-propynyl | 3 |
| 72 | 3-F | 2-propynyl | 3 |
| 73 | 4-F | H | 2 |
| 74 | 4-F | CH₃ | 2 |
| 75 | 4-F | CH₂CH₃ | 2 |
| 76 | 4-F | CH₂CH₂CH₃ | 2 |
| 77 | 4-F | CH(CH₃)₂ | 2 |
| 78 | 4-F | vinyl | 2 |
| 79 | 4-F | allyl | 2 |
| 80 | 4-F | 1-propenyl | 2 |
| 81 | 4-F | isopropenyl | 2 |
| 82 | 4-F | ethynyl | 2 |
| 83 | 4-F | 1-propynyl | 2 |
| 84 | 4-F | 2-propynyl | 2 |
| 85 | 4-F | H | 3 |
| 86 | 4-F | CH₃ | 3 |
| 87 | 4-F | CH₂CH₃ | 3 |
| 88 | 4-F | CH₂CH₂CH₃ | 3 |
| 89 | 4-F | CH(CH₃)₂ | 3 |
| 90 | 4-F | vinyl | 3 |
| 91 | 4-F | allyl | 3 |
| 92 | 4-F | 1-propenyl | 3 |
| 93 | 4-F | isopropenyl | 3 |
| 94 | 4-F | ethynyl | 3 |
| 95 | 4-F | 1-propynyl | 3 |
| 96 | 4-F | 2-propynyl | 3 |
| 97 | 2-Cl | H | 2 |
| 98 | 2-Cl | CH₃ | 2 |
| 99 | 2-Cl | CH₂CH₃ | 2 |
| 100 | 2-Cl | CH₂CH₂CH₃ | 2 |
| 101 | 2-Cl | CH(CH₃)₂ | 2 |
| 102 | 2-Cl | vinyl | 2 |
| 103 | 2-Cl | allyl | 2 |
| 104 | 2-Cl | 1-propenyl | 2 |
| 105 | 2-Cl | isopropenyl | 2 |
| 106 | 2-Cl | ethynyl | 2 |
| 107 | 2-Cl | 1-propynyl | 2 |
| 108 | 2-Cl | 2-propynyl | 2 |
| 109 | 2-Cl | H | 3 |
| 110 | 2-Cl | CH₃ | 3 |
| 111 | 2-Cl | CH₂CH₃ | 3 |
| 112 | 2-Cl | CH₂CH₂CH₃ | 3 |
| 113 | 2-Cl | CH(CH₃)₂ | 3 |
| 114 | 2-Cl | vinyl | 3 |
| 115 | 2-Cl | allyl | 3 |
| 116 | 2-Cl | 1-propenyl | 3 |
| 117 | 2-Cl | isopropenyl | 3 |
| 118 | 2-Cl | ethynyl | 3 |
| 119 | 2-Cl | 1-propynyl | 3 |
| 120 | 2-Cl | 2-propynyl | 3 |
| 121 | 3-Cl | H | 2 |
| 122 | 3-Cl | CH₃ | 2 |
| 123 | 3-Cl | CH₂CH₃ | 2 |
| 124 | 3-Cl | CH₂CH₂CH₃ | 2 |
| 125 | 3-Cl | CH(CH₃)₂ | 2 |
| 126 | 3-Cl | vinyl | 2 |
| 127 | 3-Cl | allyl | 2 |
| 128 | 3-Cl | 1-propenyl | 2 |
| 129 | 3-Cl | isopropenyl | 2 |
| 130 | 3-Cl | ethynyl | 2 |
| 131 | 3-Cl | 1-propynyl | 2 |
| 132 | 3-Cl | 2-propynyl | 2 |
| 133 | 3-Cl | H | 3 |
| 134 | 3-Cl | CH₃ | 3 |

TABLE 1-continued

[Structure: R¹-substituted phenyl attached to N of pyrrolidinone with C=O; 3-position has CH₂ linked to piperazine N, other piperazine N connected to (CH₂)ₙOR²]

| Compound No. | R¹ | R² | n |
|---|---|---|---|
| 135 | 3-Cl | CH₂CH₃ | 3 |
| 136 | 3-Cl | CH₂CH₂CH₃ | 3 |
| 137 | 3-Cl | CH(CH₃)₂ | 3 |
| 138 | 3-Cl | vinyl | 3 |
| 139 | 3-Cl | allyl | 3 |
| 140 | 3-Cl | 1-propenyl | 3 |
| 141 | 3-Cl | isopropenyl | 3 |
| 142 | 3-Cl | ethynyl | 3 |
| 143 | 3-Cl | 1-propynyl | 3 |
| 144 | 3-Cl | 2-propynyl | 3 |
| 145 | 4-Cl | H | 2 |
| 146 | 4-Cl | CH₃ | 2 |
| 147 | 4-Cl | CH₂CH₃ | 2 |
| 148 | 4-Cl | CH₂CH₂CH₃ | 2 |
| 149 | 4-Cl | CH(CH₃)₂ | 2 |
| 150 | 4-Cl | vinyl | 2 |
| 151 | 4-Cl | allyl | 2 |
| 152 | 4-Cl | 1-propenyl | 2 |
| 153 | 4-Cl | isopropenyl | 2 |
| 154 | 4-Cl | ethynyl | 2 |
| 155 | 4-Cl | 1-propynyl | 2 |
| 156 | 4-Cl | 2-propynyl | 2 |
| 157 | 4-Cl | H | 3 |
| 158 | 4-Cl | CH₃ | 3 |
| 159 | 4-Cl | CH₂CH₃ | 3 |
| 160 | 4-Cl | CH₂CH₂CH₃ | 3 |
| 161 | 4-Cl | CH(CH₃)₂ | 3 |
| 162 | 4-Cl | vinyl | 3 |
| 163 | 4-Cl | allyl | 3 |
| 164 | 4-Cl | 1-propenyl | 3 |
| 165 | 4-Cl | isopropenyl | 3 |
| 166 | 4-Cl | ethynyl | 3 |
| 167 | 4-Cl | 1-propynyl | 3 |
| 168 | 4-Cl | 2-propynyl | 3 |
| 169 | 2-Br | H | 2 |
| 170 | 2-Br | CH₃ | 2 |
| 171 | 2-Br | CH₂CH₃ | 2 |
| 172 | 2-Br | CH₂CH₂CH₃ | 2 |
| 173 | 2-Br | CH(CH₃)₂ | 2 |
| 174 | 2-Br | vinyl | 2 |
| 175 | 2-Br | allyl | 2 |
| 176 | 2-Br | 1-propenyl | 2 |
| 177 | 2-Br | isopropenyl | 2 |
| 178 | 2-Br | ethynyl | 2 |
| 179 | 2-Br | 1-propynyl | 2 |
| 180 | 2-Br | 2-propynyl | 2 |
| 181 | 2-Br | H | 3 |
| 182 | 2-Br | CH₃ | 3 |
| 183 | 2-Br | CH₂CH₃ | 3 |
| 184 | 2-Br | CH₂CH₂CH₃ | 3 |
| 185 | 2-Br | CH(CH₃)₂ | 3 |
| 186 | 2-Br | vinyl | 3 |
| 187 | 2-Br | allyl | 3 |
| 188 | 2-Br | 1-propenyl | 3 |
| 189 | 2-Br | isopropenyl | 3 |
| 190 | 2-Br | ethynyl | 3 |
| 191 | 2-Br | 1-propynyl | 3 |
| 192 | 2-Br | 2-propynyl | 3 |
| 193 | 3-Br | H | 2 |
| 194 | 3-Br | CH₃ | 2 |
| 195 | 3-Br | CH₂CH₃ | 2 |
| 196 | 3-Br | CH₂CH₂CH₃ | 2 |
| 197 | 3-Br | CH(CH₃)₂ | 2 |
| 198 | 3-Br | vinyl | 2 |
| 199 | 3-Br | allyl | 2 |
| 200 | 3-Br | 1-propenyl | 2 |
| 201 | 3-Br | isopropenyl | 2 |
| 202 | 3-Br | ethynyl | 2 |
| 203 | 3-Br | 1-propynyl | 2 |
| 204 | 3-Br | 2-propynyl | 2 |
| 205 | 3-Br | H | 3 |
| 206 | 3-Br | CH₃ | 3 |
| 207 | 3-Br | CH₂CH₃ | 3 |
| 208 | 3-Br | CH₂CH₂CH₃ | 3 |
| 209 | 3-Br | CH(CH₃)₂ | 3 |
| 210 | 3-Br | vinyl | 3 |
| 211 | 3-Br | allyl | 3 |
| 212 | 3-Br | 1-propenyl | 3 |
| 213 | 3-Br | isopropenyl | 3 |
| 214 | 3-Br | ethynyl | 3 |
| 215 | 3-Br | 1-propynyl | 3 |
| 216 | 3-Br | 2-propynyl | 3 |
| 217 | 4-Br | H | 2 |
| 218 | 4-Br | CH₃ | 2 |
| 219 | 4-Br | CH₂CH₃ | 2 |
| 220 | 4-Br | CH₂CH₂CH₃ | 2 |
| 221 | 4-Br | CH(CH₃)₂ | 2 |
| 222 | 4-Br | vinyl | 2 |
| 223 | 4-Br | allyl | 2 |
| 224 | 4-Br | 1-propenyl | 2 |
| 225 | 4-Br | isopropenyl | 2 |
| 226 | 4-Br | ethynyl | 2 |
| 227 | 4-Br | 1-propynyl | 2 |
| 228 | 4-Br | 2-propynyl | 2 |
| 229 | 4-Br | H | 3 |
| 230 | 4-Br | CH₃ | 3 |
| 231 | 4-Br | CH₂CH₃ | 3 |
| 232 | 4-Br | CH₂CH₂CH₃ | 3 |
| 233 | 4-Br | CH(CH₃)₂ | 3 |
| 234 | 4-Br | vinyl | 3 |
| 235 | 4-Br | allyl | 3 |
| 236 | 4-Br | 1-propenyl | 3 |
| 237 | 4-Br | isopropenyl | 3 |
| 238 | 4-Br | ethynyl | 3 |
| 239 | 4-Br | 1-propynyl | 3 |
| 240 | 4-Br | 2-propynyl | 3 |
| 241 | 2-I | H | 2 |
| 242 | 2-I | CH₃ | 2 |
| 243 | 2-I | CH₂CH₃ | 2 |
| 244 | 2-I | CH₂CH₂CH₃ | 2 |
| 245 | 2-I | CH(CH₃)₂ | 2 |
| 246 | 2-I | vinyl | 2 |
| 247 | 2-I | allyl | 2 |
| 248 | 2-I | 1-propenyl | 2 |
| 249 | 2-I | isopropenyl | 2 |
| 250 | 2-I | ethynyl | 2 |
| 251 | 2-I | 1-propynyl | 2 |
| 252 | 2-I | 2-propynyl | 2 |
| 253 | 2-I | H | 3 |
| 254 | 2-I | CH₃ | 3 |
| 255 | 2-I | CH₂CH₃ | 3 |
| 256 | 2-I | CH₂CH₂CH₃ | 3 |
| 257 | 2-I | CH(CH₃)₂ | 3 |
| 258 | 2-I | vinyl | 3 |
| 259 | 2-I | allyl | 3 |
| 260 | 2-I | 1-propenyl | 3 |
| 261 | 2-I | isopropenyl | 3 |
| 262 | 2-I | ethynyl | 3 |
| 263 | 2-I | 1-propynyl | 3 |
| 264 | 2-I | 2-propynyl | 3 |
| 265 | 3-I | H | 2 |
| 266 | 3-I | CH₃ | 2 |
| 267 | 3-I | CH₂CH₃ | 2 |
| 268 | 3-I | CH₂CH₂CH₃ | 2 |

TABLE 1-continued

| Compound No. | R¹ | R² | n |
|---|---|---|---|
| 269 | 3-I | CH(CH₃)₂ | 2 |
| 270 | 3-I | vinyl | 2 |
| 271 | 3-I | allyl | 2 |
| 272 | 3-I | 1-propenyl | 2 |
| 273 | 3-I | isopropenyl | 2 |
| 274 | 3-I | ethynyl | 2 |
| 275 | 3-I | 1-propynyl | 2 |
| 276 | 3-I | 2-propynyl | 2 |
| 277 | 3-I | H | 3 |
| 278 | 3-I | CH₃ | 3 |
| 279 | 3-I | CH₂CH₃ | 3 |
| 280 | 3-I | CH₂CH₂CH₃ | 3 |
| 281 | 3-I | CH(CH₃)₂ | 3 |
| 282 | 3-I | vinyl | 3 |
| 283 | 3-I | allyl | 3 |
| 284 | 3-I | 1-propenyl | 3 |
| 285 | 3-I | isopropenyl | 3 |
| 286 | 3-I | ethynyl | 3 |
| 287 | 3-I | 1-propynyl | 3 |
| 288 | 3-I | 2-propynyl | 3 |
| 289 | 4-I | H | 2 |
| 290 | 4-I | CH₃ | 2 |
| 291 | 4-I | CH₂CH₃ | 2 |
| 292 | 4-I | CH₂CH₂CH₃ | 2 |
| 293 | 4-I | CH(CH₃)₂ | 2 |
| 294 | 4-I | vinyl | 2 |
| 295 | 4-I | allyl | 2 |
| 296 | 4-I | 1-propenyl | 2 |
| 297 | 4-I | isopropenyl | 2 |
| 298 | 4-I | ethynyl | 2 |
| 299 | 4-I | 1-propynyl | 2 |
| 300 | 4-I | 2-propynyl | 2 |
| 301 | 4-I | H | 3 |
| 302 | 4-I | CH₃ | 3 |
| 303 | 4-I | CH₂CH₃ | 3 |
| 304 | 4-I | CH₂CH₂CH₃ | 3 |
| 305 | 4-I | CH(CH₃)₂ | 3 |
| 306 | 4-I | vinyl | 3 |
| 307 | 4-I | allyl | 3 |
| 308 | 4-I | 1-propenyl | 3 |
| 309 | 4-I | isopropenyl | 3 |
| 310 | 4-I | ethynyl | 3 |
| 311 | 4-I | 1-propynyl | 3 |
| 312 | 4-I | 2-propynyl | 3 |

TABLE 2

| Compound No. | R¹ | R² | n |
|---|---|---|---|
| 1 | 3-Cl | H | 2 |
| 2 | 3-Cl | CH₃ | 2 |
| 3 | 3-Cl | CH₂CH₃ | 2 |
| 4 | 3-Cl | CH₂CH₂CH₃ | 2 |
| 5 | 3-Cl | CH(CH₃)₂ | 2 |
| 6 | 3-Cl | vinyl | 2 |
| 7 | 3-Cl | allyl | 2 |
| 8 | 3-Cl | 1-propenyl | 2 |
| 9 | 3-Cl | isopropenyl | 2 |
| 10 | 3-Cl | ethynyl | 2 |
| 11 | 3-Cl | 1-propynyl | 2 |
| 12 | 3-Cl | 2-propynyl | 2 |
| 13 | 3-Cl | H | 3 |
| 14 | 3-Cl | CH₃ | 3 |
| 15 | 3-Cl | CH₂CH₃ | 3 |
| 16 | 3-Cl | CH₂CH₂CH₃ | 3 |
| 17 | 3-Cl | CH(CH₃)₂ | 3 |
| 18 | 3-Cl | vinyl | 3 |
| 19 | 3-Cl | allyl | 3 |
| 20 | 3-Cl | 1-propenyl | 3 |
| 21 | 3-Cl | isopropenyl | 3 |
| 22 | 3-Cl | ethynyl | 3 |
| 23 | 3-Cl | 1-propynyl | 3 |
| 24 | 3-Cl | 2-propynyl | 3 |
| 25 | 3-Cl | H | 2 |
| 26 | 3-Cl | CH₃ | 2 |
| 27 | 3-Cl | CH₂CH₃ | 2 |
| 28 | 3-Cl | CH₂CH₂CH₃ | 2 |
| 29 | 3-Cl | CH(CH₃)₂ | 2 |
| 30 | 3-Cl | vinyl | 2 |
| 31 | 3-Cl | allyl | 2 |
| 32 | 3-Cl | 1-propenyl | 2 |
| 33 | 3-Cl | isopropenyl | 2 |
| 34 | 3-Cl | ethynyl | 2 |
| 35 | 3-Cl | 1-propynyl | 2 |
| 36 | 3-Cl | 2-propynyl | 2 |
| 37 | 3-Cl | H | 3 |
| 38 | 3-Cl | CH₃ | 3 |
| 39 | 3-Cl | CH₂CH₃ | 3 |
| 40 | 3-Cl | CH₂CH₂CH₃ | 3 |
| 41 | 3-Cl | CH(CH₃)₂ | 3 |
| 42 | 3-Cl | vinyl | 3 |
| 43 | 3-Cl | allyl | 3 |
| 44 | 3-Cl | 1-propenyl | 3 |
| 45 | 3-Cl | isopropenyl | 3 |
| 46 | 3-Cl | ethynyl | 3 |
| 47 | 3-Cl | 1-propynyl | 3 |
| 48 | 3-Cl | 2-propynyl | 3 |
| 49 | 4-Cl | H | 2 |
| 50 | 4-Cl | CH₃ | 2 |
| 51 | 4-Cl | CH₂CH₃ | 2 |
| 52 | 4-Cl | CH₂CH₂CH₃ | 2 |
| 53 | 4-Cl | CH(CH₃)₂ | 2 |
| 54 | 4-Cl | vinyl | 2 |
| 55 | 4-Cl | allyl | 2 |
| 56 | 4-Cl | 1-propenyl | 2 |
| 57 | 4-Cl | isopropenyl | 2 |
| 58 | 4-Cl | ethynyl | 2 |
| 59 | 4-Cl | 1-propynyl | 2 |
| 60 | 4-Cl | 2-propynyl | 2 |
| 61 | 4-Cl | H | 3 |
| 62 | 4-Cl | CH₃ | 3 |
| 63 | 4-Cl | CH₂CH₃ | 3 |
| 64 | 4-Cl | CH₂CH₂CH₃ | 3 |
| 65 | 4-Cl | CH(CH₃)₂ | 3 |
| 66 | 4-Cl | vinyl | 3 |
| 67 | 4-Cl | allyl | 3 |
| 68 | 4-Cl | 1-propenyl | 3 |
| 69 | 4-Cl | isopropenyl | 3 |
| 70 | 4-Cl | ethynyl | 3 |
| 71 | 4-Cl | 1-propynyl | 3 |
| 72 | 4-Cl | 2-propynyl | 3 |

TABLE 2-continued

![Structure: R¹-substituted phenyl-N-pyrrolidinone-CH₂-piperazine-(CH₂)ₙ-OR², 2HCl]

| Compound No. | R¹ | R² | n |
|---|---|---|---|
| 73 | 4-Cl | H | 2 |
| 74 | 4-Cl | CH₃ | 2 |
| 75 | 4-Cl | CH₂CH₃ | 2 |
| 76 | 4-Cl | CH₂CH₂CH₃ | 2 |
| 77 | 4-Cl | CH(CH₃)₂ | 2 |
| 78 | 4-Cl | vinyl | 2 |
| 79 | 4-Cl | allyl | 2 |
| 80 | 4-Cl | 1-propenyl | 2 |
| 81 | 4-Cl | isopropenyl | 2 |
| 82 | 4-Cl | ethynyl | 2 |
| 83 | 4-Cl | 1-propynyl | 2 |
| 84 | 4-Cl | 2-propynyl | 2 |
| 85 | 4-Cl | H | 3 |
| 86 | 4-Cl | CH₃ | 3 |
| 87 | 4-Cl | CH₂CH₃ | 3 |
| 88 | 4-Cl | CH₂CH₂CH₃ | 3 |
| 89 | 4-Cl | CH(CH₃)₂ | 3 |
| 90 | 4-Cl | vinyl | 3 |
| 91 | 4-Cl | allyl | 3 |
| 92 | 4-Cl | 1-propenyl | 3 |
| 93 | 4-Cl | isopropenyl | 3 |
| 94 | 4-Cl | ethynyl | 3 |
| 95 | 4-Cl | 1-propynyl | 3 |
| 96 | 4-Cl | 2-propynyl | 3 |
| 97 | 3-Br | H | 2 |
| 98 | 3-Br | CH₃ | 2 |
| 99 | 3-Br | CH₂CH₃ | 2 |
| 100 | 3-Br | CH₂CH₂CH₃ | 2 |
| 101 | 3-Br | CH(CH₃)₂ | 2 |
| 102 | 3-Br | vinyl | 2 |
| 103 | 3-Br | allyl | 2 |
| 104 | 3-Br | 1-propenyl | 2 |
| 105 | 3-Br | isopropenyl | 2 |
| 106 | 3-Br | ethynyl | 2 |
| 107 | 3-Br | 1-propynyl | 2 |
| 108 | 3-Br | 2-propynyl | 2 |
| 109 | 3-Br | H | 3 |
| 110 | 3-Br | CH₃ | 3 |
| 111 | 3-Br | CH₂CH₃ | 3 |
| 112 | 3-Br | CH₂CH₂CH₃ | 3 |
| 113 | 3-Br | CH(CH₃)₂ | 3 |
| 114 | 3-Br | vinyl | 3 |
| 115 | 3-Br | allyl | 3 |
| 116 | 3-Br | 1-propenyl | 3 |
| 117 | 3-Br | isopropenyl | 3 |
| 118 | 3-Br | ethynyl | 3 |
| 119 | 3-Br | 1-propynyl | 3 |
| 120 | 3-Br | 2-propynyl | 3 |
| 121 | 3-Br | H | 2 |
| 122 | 3-Br | CH₃ | 2 |
| 123 | 3-Br | CH₂CH₃ | 2 |
| 124 | 3-Br | CH₂CH₂CH₃ | 2 |
| 125 | 3-Br | CH(CH₃)₂ | 2 |
| 126 | 3-Br | vinyl | 2 |
| 127 | 3-Br | allyl | 2 |
| 128 | 3-Br | 1-propenyl | 2 |
| 129 | 3-Br | isopropenyl | 2 |
| 130 | 3-Br | ethynyl | 2 |
| 131 | 3-Br | 1-propynyl | 2 |
| 132 | 3-Br | 2-propynyl | 2 |
| 133 | 3-Br | H | 3 |
| 134 | 3-Br | CH₃ | 3 |
| 135 | 3-Br | CH₂CH₃ | 3 |
| 136 | 3-Br | CH₂CH₂CH₃ | 3 |
| 137 | 3-Br | CH(CH₃)₂ | 3 |
| 138 | 3-Br | vinyl | 3 |
| 139 | 3-Br | allyl | 3 |
| 140 | 3-Br | 1-propenyl | 3 |
| 141 | 3-Br | isopropenyl | 3 |
| 142 | 3-Br | ethynyl | 3 |
| 143 | 3-Br | 1-propynyl | 3 |
| 144 | 3-Br | 2-propynyl | 3 |
| 145 | 4-Br | H | 2 |
| 146 | 4-Br | CH₃ | 2 |
| 147 | 4-Br | CH₂CH₃ | 2 |
| 148 | 4-Br | CH₂CH₂CH₃ | 2 |
| 149 | 4-Br | CH(CH₃)₂ | 2 |
| 150 | 4-Br | vinyl | 2 |
| 151 | 4-Br | allyl | 2 |
| 152 | 4-Br | 1-propenyl | 2 |
| 153 | 4-Br | isopropenyl | 2 |
| 154 | 4-Br | ethynyl | 2 |
| 155 | 4-Br | 1-propynyl | 2 |
| 156 | 4-Br | 2-propynyl | 2 |
| 157 | 4-Br | H | 3 |
| 158 | 4-Br | CH₃ | 3 |
| 159 | 4-Br | CH₂CH₃ | 3 |
| 160 | 4-Br | CH₂CH₂CH₃ | 3 |
| 161 | 4-Br | CH(CH₃)₂ | 3 |
| 162 | 4-Br | vinyl | 3 |
| 163 | 4-Br | allyl | 3 |
| 164 | 4-Br | 1-propenyl | 3 |
| 165 | 4-Br | isopropenyl | 3 |
| 166 | 4-Br | ethynyl | 3 |
| 167 | 4-Br | 1-propynyl | 3 |
| 168 | 4-Br | 2-propynyl | 3 |
| 169 | 4-Br | H | 2 |
| 170 | 4-Br | CH₃ | 2 |
| 171 | 4-Br | CH₂CH₃ | 2 |
| 172 | 4-Br | CH₂CH₂CH₃ | 2 |
| 173 | 4-Br | CH(CH₃)₂ | 2 |
| 174 | 4-Br | vinyl | 2 |
| 175 | 4-Br | allyl | 2 |
| 176 | 4-Br | 1-propenyl | 2 |
| 177 | 4-Br | isopropenyl | 2 |
| 178 | 4-Br | ethynyl | 2 |
| 179 | 4-Br | 1-propynyl | 2 |
| 180 | 4-Br | 2-propynyl | 2 |
| 181 | 4-Br | H | 3 |
| 182 | 4-Br | CH₃ | 3 |
| 183 | 4-Br | CH₂CH₃ | 3 |
| 184 | 4-Br | CH₂CH₂CH₃ | 3 |
| 185 | 4-Br | CH(CH₃)₂ | 3 |
| 186 | 4-Br | vinyl | 3 |
| 187 | 4-Br | allyl | 3 |
| 188 | 4-Br | 1-propenyl | 3 |
| 189 | 4-Br | isopropenyl | 3 |
| 190 | 4-Br | ethynyl | 3 |
| 191 | 4-Br | 1-propynyl | 3 |
| 192 | 4-Br | 2-propynyl | 3 |

TABLE 3

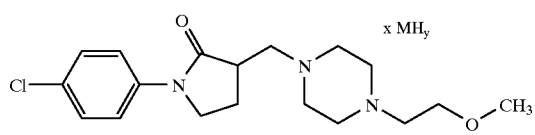

MH$_y$: Acid forming a salt with the free form of the compound
x: Molar ratio of the acid to the free form of the compound

| Compound No. | MH$_y$ | x | |
|---|---|---|---|
| 1 | Hydrochloric acid | 1 | Anhydride |
| 2 | Hydrochloric acid | 1 | Monohydrate |
| 3 | Hydrochloric acid | 1 | Dihydrate |
| 4 | Hydrochloric acid | 1 | Trihydrate |
| 5 | Hydrochloric acid | 2 | Monohydrate |
| 6 | Hydrochloric acid | 2 | Trihydrate |
| 7 | Hydrobromic acid | 1 | Anhydride |
| 8 | Hydrobromic acid | 1 | Monohydrate |
| 9 | Hydrobromic acid | 1 | Dihydrate |
| 10 | Hydrobromic acid | 1 | Trihydrate |
| 11 | Hydrobromic acid | 2 | Anhydride |
| 12 | Hydrobromic acid | 2 | Monohydrate |
| 13 | Hydrobromic acid | 2 | Dihydrate |
| 14 | Hydrobromic acid | 2 | Trihydrate |
| 15 | Hydriodic acid | 1 | Anhydride |
| 16 | Hydriodic acid | 1 | Monohydrate |
| 17 | Hydriodic acid | 1 | Dihydrate |
| 18 | Hydriodic acid | 1 | Trihydrate |
| 19 | Hydriodic acid | 2 | Anhydride |
| 20 | Hydriodic acid | 2 | Monohydrate |
| 21 | Hydriodic acid | 2 | Dihydrate |
| 22 | Hydriodic acid | 2 | Trihydrate |
| 23 | Nitric acid | 1 | Anhydride |
| 24 | Nitric acid | 1 | Monohydrate |
| 25 | Nitric acid | 1 | Dihydrate |
| 26 | Nitric acid | 1 | Trihydrate |
| 27 | Nitric acid | 2 | Anhydride |
| 28 | Nitric acid | 2 | Monohydrate |
| 29 | Nitric acid | 2 | Dihydrate |
| 30 | Nitric acid | 2 | Trihydrate |
| 31 | Sulfuric acid | 1 | Anhydride |
| 32 | Sulfuric acid | 1 | Mnohydrate |
| 33 | Sulfuric acid | 1 | Dihydrate |
| 34 | Sulfuric acid | 1 | Trihydrate |
| 35 | Sulfuric acid | 2 | Anhydride |
| 36 | Sulfuric acid | 2 | Mnohydrate |
| 37 | Sulfuric acid | 2 | Dihydrate |
| 38 | Sulfuric acid | 2 | Trihydrate |
| 39 | Phosphoric acid | 1 | Anhydride |
| 40 | Phosphoric acid | 1 | Monohydrate |
| 41 | Phosphoric acid | 1 | Dihydrate |
| 42 | Phosphoric acid | 1 | Trihydrate |
| 43 | Phosphoric acid | 2 | Anhydride |
| 44 | Phosphoric acid | 2 | Monohydrate |
| 45 | Phosphoric acid | 2 | Dihydrate |
| 46 | Phosphoric acid | 2 | Trihydrate |
| 47 | Acetic acid | 1 | Anhydride |
| 48 | Acetic acid | 1 | Monohydrate |
| 49 | Acetic acid | 1 | Dihydrate |
| 50 | Acetic acid | 1 | Trihydrate |
| 51 | Acetic acid | 2 | Anhydride |
| 52 | Acetic acid | 2 | Monohydrate |
| 53 | Acetic acid | 2 | Dihydrate |
| 54 | Acetic acid | 2 | Trihydrate |
| 55 | Fumaric acid | 1 | Anhydride |
| 56 | Fumaric acid | 1 | Monohydrate |
| 57 | Fumaric acid | 1 | Dihydrate |
| 58 | Fumaric acid | 1 | Trihydrate |
| 59 | Fumaric acid | 2 | Anhydride |
| 60 | Fumaric acid | 2 | Monohydrate |
| 61 | Fumaric acid | 2 | Dihydrate |
| 62 | Fumaric acid | 2 | Trihydrate |
| 63 | Maleic acid | 1 | Anhydride |
| 64 | Maleic acid | 1 | Monohydrate |
| 65 | Maleic acid | 1 | Dihydrate |
| 66 | Maleic acid | 1 | Trihydrate |

TABLE 3-continued

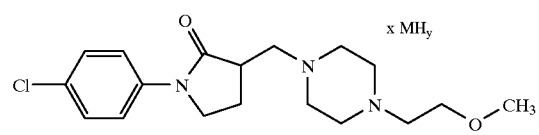

MH$_y$: Acid forming a salt with the free form of the compound
x: Molar ratio of the acid to the free form of the compound

| Compound No. | MH$_y$ | x | |
|---|---|---|---|
| 67 | Maleic acid | 2 | Anhydride |
| 68 | Maleic acid | 2 | Monohydrate |
| 69 | Maleic acid | 2 | Dihydrate |
| 70 | Maleic acid | 2 | Trihydrate |
| 71 | Succinic acid | 1 | Anhydride |
| 72 | Succinic acid | 1 | Mnohydrate |
| 73 | Succinic acid | 1 | Dihydrate |
| 74 | Succinic acid | 1 | Trihydrate |
| 75 | Succinic acid | 2 | Anhydride |
| 76 | Succinic acid | 2 | Mnohydrate |
| 77 | Succinic acid | 2 | Dihydrate |
| 78 | Succinic acid | 2 | Trihydrate |
| 79 | Citric acid | 1 | Anhydride |
| 80 | Citric acid | 1 | Monohydrate |
| 81 | Citric acid | 1 | Dihydrate |
| 82 | Citric acid | 1 | Trihydrate |
| 83 | Citric acid | 2 | Anhydride |
| 84 | Citric acid | 2 | Monohydrate |
| 85 | Citric acid | 2 | Dihydrate |
| 86 | Citric acid | 2 | Trihydrate |
| 87 | Citric acid | 3 | Anhydride |
| 88 | Citric acid | 3 | Monohydrate |
| 89 | Citric acid | 3 | Dihydrate |
| 90 | Citric acid | 3 | Trihydrate |
| 91 | Benzoic acid | 1 | Anhydride |
| 92 | Benzoic acid | 1 | Monohydrate |
| 93 | Benzoic acid | 1 | Dihydrate |
| 94 | Benzoic acid | 1 | Trihydrate |
| 95 | Benzoic acid | 2 | Anhydride |
| 96 | Benzoic acid | 2 | Monohydrate |
| 97 | Benzoic acid | 2 | Dihydrate |
| 98 | Benzoic acid | 2 | Trihydrate |
| 99 | Trifluoroacetic acid | 1 | Anhydride |
| 100 | Trifluoroacetic acid | 1 | Monohydrate |
| 101 | Trifluoroacetic acid | 1 | Dihydrate |
| 102 | Trifluoroacetic acid | 1 | Trihydrate |
| 103 | Trifluoroacetic acid | 2 | Anhydride |
| 104 | Trifluoroacetic acid | 2 | Monohydrate |
| 105 | Trifluoroacetic acid | 2 | Dihydrate |
| 106 | Trifluoroacetic acid | 2 | Trihydrate |
| 107 | Methanesulfonic acid | 1 | Anhydride |
| 108 | Methanesulfonic acid | 1 | Monohydrate |
| 109 | Methanesulfonic acid | 1 | Dihydrate |
| 110 | Methanesulfonic acid | 1 | Trihydrate |
| 111 | Methanesulfonic acid | 2 | Anhydride |
| 112 | Methanesulfonic acid | 2 | Monohydrate |
| 113 | Methanesulfonic acid | 2 | Dihydrate |
| 114 | Methanesulfonic acid | 2 | Trihydrate |
| 115 | Ethanesulfonic acid | 1 | Anhydride |
| 116 | Ethanesulfonic acid | 1 | Monohydrate |
| 117 | Ethanesulfonic acid | 1 | Dihydrate |
| 118 | Ethanesulfonic acid | 1 | Trihydrate |
| 119 | Ethanesulfonic acid | 2 | Anhydride |
| 120 | Ethanesulfonic acid | 2 | Monohydrate |
| 121 | Ethanesulfonic acid | 2 | Dihydrate |
| 122 | Ethanesulfonic acid | 2 | Trihydrate |
| 123 | p-Toluenesulfonic acid | 1 | Anhydride |
| 124 | p-Toluenesulfonic acid | 1 | Monohydrate |
| 125 | p-Toluenesulfonic acid | 1 | Dihydrate |
| 126 | p-Toluenesulfonic acid | 1 | Trihydrate |
| 127 | p-Toluenesulfonic acid | 2 | Anhydride |
| 128 | p-Toluenesulfonic acid | 2 | Monohydrate |
| 129 | p-Toluenesulfonic acid | 2 | Dihydrate |
| 130 | p-Toluenesulfonic acid | 2 | Trihydrate |
| 131 | Benzenesulfonic acid | 1 | Anhydride |
| 132 | Benzenesulfonic acid | 1 | Monohydrate |

TABLE 3-continued

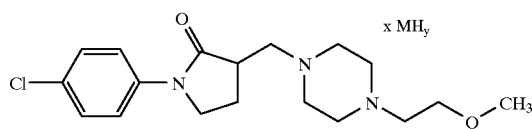

MH$_y$: Acid forming a salt with the free form of the compound
x: Molar ratio of the acid to the free form of the compound

| Compound No. | MH$_y$ | x | |
|---|---|---|---|
| 133 | Benzenesulfonic acid | 1 | Dihydrate |
| 134 | Benzenesulfonic acid | 1 | Trihydrate |
| 135 | Benzenesulfonic acid | 2 | Anhydride |
| 136 | Benzenesulfonic acid | 2 | Monohydrate |
| 137 | Benzenesulfonic acid | 2 | Dihydrate |
| 138 | Benzenesulfonic acid | 2 | Trihydrate |
| 139 | Benzenesulfonic acid | 2 | 3.5 Hydrate |
| 140 | L-Lactic acid | 1 | Anhydride |
| 141 | L-Lactic acid | 1 | Monohydrate |
| 142 | L-Lactic acid | 1 | Dihydrate |
| 143 | L-Lactic acid | 1 | Trihydrate |
| 144 | L-Lactic acid | 2 | Anhydride |
| 145 | L-Lactic acid | 2 | Monohydrate |
| 146 | L-Lactic acid | 2 | Dihydrate |
| 147 | L-Lactic acid | 2 | Trihydrate |
| 148 | (R)-Mandelic acid | 1 | Anhydride |
| 149 | (R)-Mandelic acid | 1 | Monohydrate |
| 150 | (R)-Mandelic acid | 1 | Dihydrate |
| 151 | (R)-Mandelic acid | 1 | Trihydrate |
| 152 | (R)-Mandelic acid | 2 | Anhydride |
| 153 | (R)-Mandelic acid | 2 | Monohydrate |
| 154 | (R)-Mandelic acid | 2 | Dihydrate |
| 155 | (R)-Mandelic acid | 2 | Trihydrate |
| 156 | (S)-Mandelic acid | 1 | Anhydride |
| 157 | (S)-Mandelic acid | 1 | Monohydrate |
| 158 | (S)-Mandelic acid | 1 | Dihydrate |
| 159 | (S)-Mandelic acid | 1 | Trihydrate |
| 160 | (S)-Mandelic acid | 2 | Anhydride |
| 161 | (S)-Mandelic acid | 2 | Monohydrate |
| 162 | (S)-Mandelic acid | 2 | Dihydrate |
| 163 | (S)-Mandelic acid | 2 | Trihydrate |
| 164 | (+)-Camphanic acid | 1 | Anhydride |
| 165 | (+)-Camphanic acid | 1 | Monohydrate |
| 166 | (+)-Camphanic acid | 1 | Dihydrate |
| 167 | (+)-Camphanic acid | 1 | Trihydrate |
| 168 | (+)-Camphanic acid | 2 | Anhydride |
| 169 | (+)-Camphanic acid | 2 | Monohydrate |
| 170 | (+)-Camphanic acid | 2 | Dihydrate |
| 171 | (+)-Camphanic acid | 2 | Trihydrate |
| 172 | (−)-Camphanic acid | 1 | Anhydride |
| 173 | (−)-Camphanic acid | 1 | Monohydrate |
| 174 | (−)-Camphanic acid | 1 | Dihydrate |
| 175 | (−)-Camphanic acid | 1 | Trihydrate |
| 176 | (−)-Camphanic acid | 2 | Anhydride |
| 177 | (−)-Camphanic acid | 2 | Monohydrate |
| 178 | (−)-Camphanic acid | 2 | Dihydrate |
| 179 | (−)-Camphanic acid | 2 | Trihydrate |
| 180 | L-Tartaric acid | 1 | Anhydride |
| 181 | L-Tartaric acid | 1 | Monohydrate |
| 182 | L-Tartaric acid | 1 | Dihydrate |
| 183 | L-Tartaric acid | 1 | Trihydrate |
| 184 | L-Tartaric acid | 2 | Anhydride |
| 185 | L-Tartaric acid | 2 | Monohydrate |
| 186 | L-Tartaric acid | 2 | Dihydrate |
| 187 | L-Tartaric acid | 2 | Trihydrate |
| 188 | D-Tartaric acid | 1 | Anhydride |
| 189 | D-Tartaric acid | 1 | Monohydrate |
| 190 | D-Tartaric acid | 1 | Dihydrate |
| 191 | D-Tartaric acid | 1 | Trihydrate |
| 192 | D-Tartaric acid | 2 | Anhydride |
| 193 | D-Tartaric acid | 2 | Monohydrate |
| 194 | D-Tartaric acid | 2 | Dihydrate |
| 195 | D-Tartaric acid | 2 | Trihydrate |
| 196 | Dibenzoyl-L-tartaric acid | 1 | Anhydride |
| 197 | Dibenzoyl-L-tartaric acid | 1 | Monohydrate |
| 198 | Dibenzoyl-L-tartaric acid | 1 | Dihydrate |

TABLE 3-continued

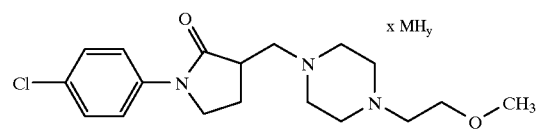

MH$_y$: Acid forming a salt with the free form of the compound
x: Molar ratio of the acid to the free form of the compound

| Compound No. | MH$_y$ | x | |
|---|---|---|---|
| 199 | Dibenzoyl-L-tartaric acid | 1 | Trihydrate |
| 200 | Dibenzoyl-L-tartaric acid | 2 | Anhydride |
| 201 | Dibenzoyl-L-tartaric acid | 2 | Monohydrate |
| 202 | Dibenzoyl-L-tartaric acid | 2 | Dihydrate |
| 203 | Dibenzoyl-L-tartaric acid | 2 | Trihydrate |
| 204 | Dibenzoyl-D-tartaric acid | 1 | Anhydride |
| 205 | Dibenzoyl-D-tartaric acid | 1 | Monohydrate |
| 206 | Dibenzoyl-D-tartaric acid | 1 | Dihydrate |
| 207 | Dibenzoyl-D-tartaric acid | 1 | Trihydrate |
| 208 | Dibenzoyl-D-tartaric acid | 2 | Anhydride |
| 209 | Dibenzoyl-D-tartaric acid | 2 | Monohydrate |
| 210 | Dibenzoyl-D-tartaric acid | 2 | Dihydrate |
| 211 | Dibenzoyl-D-tartaric acid | 2 | Trihydrate |
| 212 | Di-p-toluoyl-L-Tartaric acid | 1 | Anhydride |
| 213 | Di-p-toluoyl-L-Tartaric acid | 1 | Monohydrate |
| 214 | Di-p-toluoyl-L-Tartaric acid | 1 | Dihydrate |
| 215 | Di-p-toluoyl-L-Tartaric acid | 1 | Trihydrate |
| 216 | Di-p-toluoyl-L-Tartaric acid | 2 | Anhydride |
| 217 | Di-p-toluoyl-L-Tartaric acid | 2 | Monohydrate |
| 218 | Di-p-toluoyl-L-Tartaric acid | 2 | Dihydrate |
| 219 | Di-p-toluoyl-L-Tartaric acid | 2 | Trihydrate |
| 220 | Di-p-toluoyl-D-Tartaric acid | 1 | Anhydride |
| 221 | Di-p-toluoyl-D-Tartaric acid | 1 | Monohydrate |
| 222 | Di-p-toluoyl-D-Tartaric acid | 1 | Dihydrate |
| 223 | Di-p-toluoyl-D-Tartaric acid | 1 | Trihydrate |
| 224 | Di-p-toluoyl-D-Tartaric acid | 2 | Anhydride |
| 225 | Di-p-toluoyl-D-Tartaric acid | 2 | Monohydrate |
| 226 | Di-p-toluoyl-D-Tartaric acid | 2 | Dihydrate |
| 227 | Di-p-toluoyl-D-Tartaric acid | 2 | Trihydrate |
| 228 | (+)-10-Camphorsulfonic acid | 1 | |
| 229 | (+)-10-Camphorsulfonic acid | 2 | |
| 230 | (−)-10-Camphorsulfonic acid | 1 | |
| 231 | (−)-10-Camphorsulfonic acid | 2 | |
| 232 | (R)-Thiazolidine-4-carboxylic acid | 1 | |
| 233 | (R)-Thiazolidine-4-carboxylic acid | 2 | |
| 234 | D-3-Phenyllactic acid | 1 | |
| 235 | D-3-Phenyllactic acid | 2 | |
| 236 | L-3-Phenyllactic acid | 1 | |
| 237 | L-3-Phenyllactic acid | 2 | |
| 238 | (−)-Bromocamphor-8-sulfonic acid | 1 | |
| 239 | (−)-Bromocamphor-8-sulfonic acid | 2 | |
| 240 | (+)-Bromocamphor-8-sulfonic acid | 1 | |
| 241 | (+)-Bromocamphor-8-sulfonic acid | 2 | |
| 242 | (R)-2-Pyroglutamic acid | 1 | |
| 243 | (R)-2-Pyroglutamic acid | 2 | |
| 244 | (S)-2-Pyroglutamic acid | 1 | |
| 245 | (S)-2-Pyroglutamic acid | 2 | |
| 246 | (+)-2'-Nitrotartronic acid | 1 | |
| 247 | (+)-2'-Nitrotartronic acid | 2 | |
| 248 | (−)-2'-Nitrotartronic acid | 1 | |
| 249 | (−)-2'-Nitrotartronic acid | 2 | |
| 250 | L-Malic acid | 1 | |
| 251 | L-Malic acid | 2 | |
| 252 | D-Malic acid | 1 | |
| 253 | D-Malic acid | 2 | |
| 254 | L-Phenylglycine | 1 | |
| 255 | L-Phenylglycine | 2 | |
| 256 | D-Phenylglycine | 1 | |
| 257 | D-Phenylglycine | 2 | |
| 258 | L-Phenylalanine | 1 | |
| 259 | L-Phenylalanine | 2 | |
| 260 | D-Phenylalanine | 1 | |
| 261 | D-Phenylalanine | 2 | |
| 262 | Benzoyl-L-tartaric acid | 1 | |

TABLE 3-continued

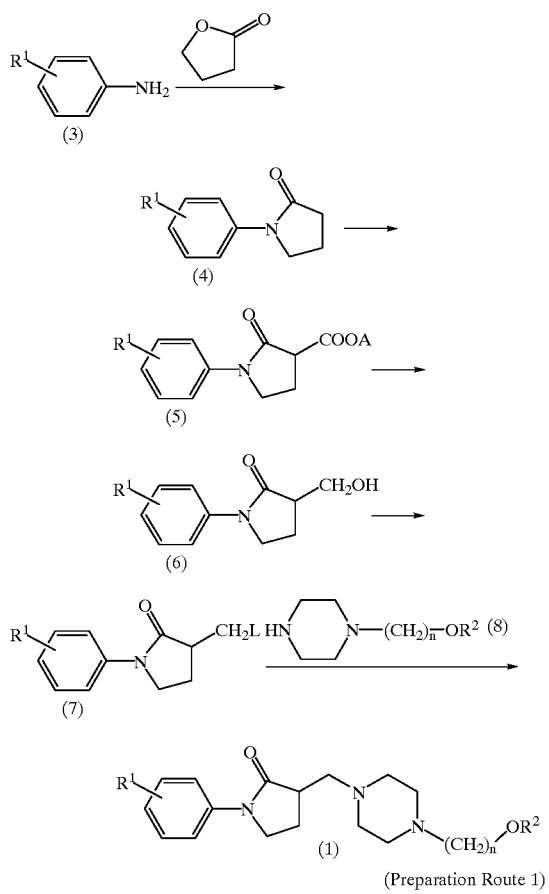

MH$_y$: Acid forming a salt with the free form of the compound
x: Molar ratio of the acid to the free form of the compound

| Compound No. | MH$_y$ | x |
|---|---|---|
| 263 | Benzoyl-L-tartaric acid | 2 |
| 264 | Benzoyl-D-tartaric acid | 1 |
| 265 | Benzoyl-D-tartaric acid | 2 |

Typical preparation methods for the compounds of this invention will be described. First, the compound represented by general formula (1) may be prepared, for example, via the following Preparation Route 1:

(Preparation Route 1)

wherein R$^1$, R$^2$ and n are as defined in general formula (1); A is methyl or ethyl; L is a halogen, tosyloxy or mesyloxy.

Compound (4) may be prepared by dehydrating an aniline derivative represented by general formula (3) with γ-butyrolactone. The reaction may be conducted with no solvent; at 50 to 250° C., preferably 150 to 200° C.; for 5 to 20 hours, preferably 10 to 15 hours. If necessary, an acid catalyst such as hydrochloric acid can be added.

Compound (5) may be prepared by alkoxycarbonylating Compound (4) in an inert solvent in the presence of a base. They can be reacted at 30 to 200° C., preferably 70 to 150° C. for 3 to 20 hours, preferably 5 to 15 hours. Inert solvents which may be used include aromatic hydrocarbons such as benzene, toluene and xylenes; ethers such as tetrahydrofuran, 1,4-dioxane, butyl ether, ethyleneglycol dimethyl ether; and alcohols such as methanol, ethanol and propanol. Reaction agents for alkoxycarbonylation include esters such as dimethyl carbonate, diethyl carbonate, ethyl phosphonoformate and diethyl oxalate. The base includes inorganic bases such as potassium carbonate, sodium carbonate, sodium amide and sodium hydride; and organic bases such as triethylamine, tripropylamine, pyridine, 1,8-diazabicyclo[5.4.0]undec-7-ene(DBU), potassium tert-butoxide.

Compound (6) may be prepared by reducing Compound (5) in an inert solvent at −75 to 200° C., preferably 0 to 100° C., for 1 to 20 hours, more preferably 5 to 15 hours. Inert-solvents which may be used include aromatic hydrocarbons such as benzene and toluene; ethers such as diethyl ether, tetrahydrofuran, 1,4-dioxane, 1,2-dimethoxyethane and ethylene glycol dimethyl ether; halogenated hydrocarbons such as dichloromethane, chloroform and 1,2-dichloroethane; alcohols such as methanol and ethanol; these may be used solely or in combination. Reducing agents which may be used include aluminum hydride, lithium aluminum hydride, sodium borohydride, and combinations of lithium aluminum hydride and aluminum chloride, of sodium borohydride and calcium chloride, and of sodium borohydride and aluminum chloride.

Compound (7) may be prepared by converting Compound (6) to a corresponding halomethyl compound with a thionyl halide or a phosphorous halide, or to a corresponding tosyl or mesyl ester with a tosyl or mesyl halide. The reaction is preferably conducted in an inert organic solvent such as chloroform, dichloromethane, tetrahydrofuran or N,N-dimethylformamide at room temperature to the boiling point of the solvent used. A halomethyl compound or a tosyl or mesyl ester formed as an intermediate may be isolated or be in situ subject to a further reaction.

Reaction of Compound (7) with an amine represented by general formula (8) will give the desired compound of general formula (1). This reaction may be conducted in tetrahydrofuran, 1,4-dioxane, acetonitrile or N,N-dimethylformamide. Reaction temperature may be 50 to 150° C., whereas individual conditions depend on basicity of the amine used and the boiling point of the system. Bases which may be used include inorganic bases such as potassium carbonate, sodium carbonate, sodium hydroxide, sodium hydrogen carbonate, sodium amide and sodium hydride, and organic bases such as triethylamine, tripropylamine, pyridine, 1,8-diazabicyclo[5.4.0]undec-7-ene(DBU). This reaction may be conducted in an excess amount of amine with no other solvents.

To the reaction may be, if necessary, added an alkali metal iodide such as potassium iodide and sodium iodide as a reaction accelerator. A molar ratio of the compound represented by formula (8) to the compound represented by formula (7) may be, but not limited to, at least one, preferably 1 to 5.

The compound represented by formula (8) may be prepared, for example, via the following Preparation Route (2).

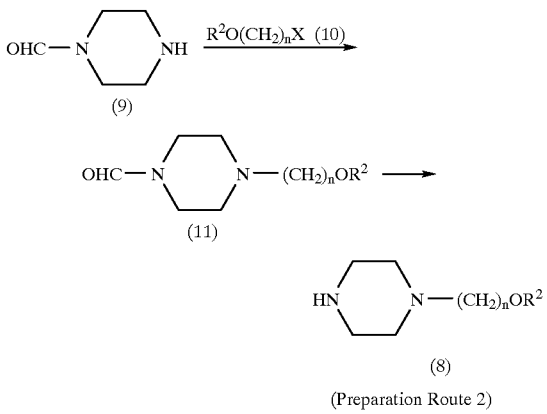

(Preparation Route 2)

wherein R² and n are as defined in general formula (1); and X is chlorine, bromine or iodine.

A formylpipecrazine represented by formula (9) may be reacted with a halide represented by general formula (10) in the presence of a base such as potassium carbonate and sodium carbonate in appropriate solvent such as an alcohol, at 30 to 150° C., preferably 50 to 100° C. for 1 to 15 hours, more preferably 3 to 10 hours, to give the compound represented by general formula (11). In this reaction, the molar ratio of the compound represented by general formula (10) to formylpiperazine is 1 to 2, preferably 1.

Compound (11) may be subject to deprotection by treatment with an acid such as hydrochloric acid/1,4-dioxane or a base such as sodium hydroxide in solvent such as methanol, to give the compound of general formula (8).

The compound represented by formula (8) may be prepared by reacting a hydroxyalkylated piperazine whose amino group is protected with tert-butoxycarbonyl group, with an alkyl halide in the presence of a base, and then deprotecting the product. Bases which may be used in the alkylation include sodium amide, potassium carbonate, triethylamine, sodium hydroxide, barium oxide, silver oxide and sodium hydride. Solvents which may be used include dimethylsulfoxide, N,N-dimethylformamide, 1,2-dimethoxyethane and tetrahydrofuran. The reaction may be conducted at 0° C. to the boiling point of the solvent for tens of minutes to 24 hours.

The optically active compound of general formula (2) may be isolated from the racemic modification of the compound represented by general formula (1) thus obtained, using an optical resolution agent. Specifically, the optical resolution may be conducted by reacting the racemic modification of the pyrrolidinone derivative with an optical resolution agent to form diastereomer salts and separating the desired optically active pyrrolidinone derivative, utilizing the difference in solubility between the diastereomer salts.

Optical resolution agents which may be used include optically active dibenzoyltartaric acid, optically active 10-camphorsulfonic acid, optically active di-p-toluoyltartaric acid, optically active tartaric acid, optically active thiazolidine-4-carboxylic acid, optically active 3-phenyl lactic acid, optically active mandelic acid, optically active camphor acid, optically active 3-bromocamphor-8-sulfonic acid, optically active pyroglutamic acid, optically active 2'-nitrotartronic acid, optically active malic acid, optically active N-acetylphenylglycine, optically active N-acetylphenylalanine and optically active camphanic acid; preferably optically active mandelic acid, optically active tartaric acid, optically active dibenzoyltartaric acid and optically active di-p-toluoyltartaric acid; most preferably optically active mandelic acid or optically active tartaric acid.

The molar ratio of the optical resolution agent to the racemic modification of the pyrrolidinone is 0.5 to 2.0, preferably 0.9 to 1.1. Solvents which may be used include acetone, methyl ethyl ketone, acetonitrile, 1,4-dioxane, ethyl acetate, methyl acetate, propyl acetate, methanol, ethanol, isopropyl alcohol and a mixture thereof. The diastereomer may be crystallized at 0 to 50° C., preferably 10 to 30° C.

The diastereomer salt obtained may be separated by filtration to give (R)- or (S)-isomer with a high optical purity. For further increasing its optical purity, it may be repeatedly recrystallized. Solvent for recrystallization is preferably, but not limited to, ethyl acetate, ethanol or methanol.

The desired optically active compound from the diastereomer salt may be readily prepared by suspending or dissolving the diastereomer salt in water, treating it with a base such as sodium hydroxide, potassium hydroxide, sodium carbonate and sodium hydrogen carbonate to desalt it, and filtrating or extracting the optically active pyrrolidinone derivative formed.

The compound of this invention represented by general formula (1) may readily form a salt with a common pharmaceutically-acceptable acid. Acids which may be used include inorganic acids such as hydrochloric acid, hydrobromic acid, hydriodic acid, nitric acid, sulfuric acid and phosphoric acid; and organic acids such as acetic acid, fumaric acid, maleic acid, succinic acid, citric acid, benzoic acid, trifluoroacetic acid, methanesulfonic acid, ethanesulfonic acid, p-toluenesulfonic acid, benzenesulfonic acid, optically active lactic acid, optically active mandelic acid, optically active camphanic acid, optically active camphor acid, optically active tartaric acid, optically active benzoyltartaric acid, optically active dibenzoyltartaric acid and amino acids.

When using a monobasic or dibasic acid, a salt whose composition ratio, i.e., the ratio of the free form of the compound of general formula (1) to the acid used, is 1:1 or 1:2, can be prepared, respectively.

When a salt of a compound of the general formula (1) with optically active mandelic acid or optically active tartaric acid is used as an active ingredient in a pharmaceutical composition, the salt can be directly produced by optical resolution using optically active mandelic acid or optically active tartaric acid without desalting of the corresponding diastereomeric salt. When an optical resolution agent other than optically active mandelic acid and optically active tartaric acid is used, desalting of the corresponding diastereomeric salt and formation of the salt with optically active mandelic acid or optically active tartaric acid are necessary. However, these procedures can be omitted by the optical resolution using optically active mandelic acid or optically active tartaric acid.

A hydrate of the salt of the compound of general formula (1) may be prepared by maintaining the salt at 10 to 80° C., preferably 20 to 60° C., more preferably 25 to 40° C., under a relative humidity of 50 to 90%, preferably 60 to 80%, for 3 hours to 1 week, preferably 6 hours to 2 days.

Alternatively, a hydrate may be prepared by forming the salt in an aqueous solvent, or by recrystallizing the salt from an aqueous solvent.

Such salts and their hydrates may be also utilized as an active ingredient of this invention, as the free form of the compound of general formula (1).

The active-ingredient compounds thus obtained may be useful as an antipsychotic, which may be used in a common pharmaceutical formulation. Such a formulation may be prepared with generally used diluents or excipients such as fillers, extenders, binders, wetting agents, disintegrators, surfactants and lubricants. A variety of pharmaceutical formulations may be selected depending on a therapeutic goal; typically, tablets, pills, powders, solutions, suspensions, emulsions, granules, capsules, suppositories and injections (e.g., liquids and suspensions).

Tableting may be done with a wide variety of carriers well known in the art; for example, excipients such as lactose, sucrose, sodium chloride, dextrose, starch, calcium carbonate, kaolin, crystalline cellulose and silicic acid; binders such as water, ethanol, propanol, simple syrup, glucose solution, starch solution, gelatin solution, carboxymethyl cellulose, shellac, methyl cellulose, potassium phosphate and polyvinylpyrrolidone; disintegrators such as dry starch, sodium alginate, powdered agar, sodium bicarbonate, calcium carbonate, polyoxyethylene-sorbitan fatty acid esters, sodium lauryl sulfate, monoglyceride stearate, starch and lactose; disintegration inhibitors such as sucrose, stearic acid, cocoa butter and hydrogenated vegetable oil; absorption promoters such as quaternary ammonium bases and sodium lauryl sulfate; wetting agents such as glycerin and starch; adsorbents such as starch, lactose, kaolin, bentonite and colloidal silicic acid; and lubricants such as talc, stearates, powdered boric acid and polyethylene glycol. Furthermore, tablets may be, if necessary, coated with common coating; for example, sugar coated tablets, gelatin-encapsulated tablets, enteric-coating tablets, film-coated tablets, or bilayered or multi-layered tablets.

Pills may be prepared with a wide variety of carriers well-known in the art; for example, excipients such as glucose, lactose, starch, cacao butter, hydrogenated vegetable oil, kaolin and talc; binders such as powdered acacia, powdered tragacanth and gelatin; disintegrators such as calcium carmerose and agar.

Suppositories may be prepared with a wide variety of carriers well-known in the art such as polyethylene glycol, cacao butter, higher alcohols, higher alcohol esters, gelatin and semi-synthetic glycerides.

Capsules may be prepared as usual by filling a mixture of active ingredients with one or more of the above various carriers, in, for example, a hard or soft gelatin capsule.

Solutions, emulsions or suspensions as an injection are preferably sterilized and made to be isotonic with blood. They may be prepared with diluents commonly used in the art, such as water, ethanol, macrogol, propylene glycol, ethoxylated isostearyl alcohols, polyoxylated isostearyl alcohols and polyoxyethylene-sorbitan fatty acid esters. In this case, the pharmaceutical formulation may contain a sufficient amount of sodium chloride, dextrose or glycerin to prepare an isotonic solution, as well as common solubilizing agents, buffer agents and soothing agents.

The pharmaceutical formulation may, if necessary, contain coloring agents, preservatives, aromatics, flavoring agents, sweeteners and/or other pharmaceutical agents.

The amount of active ingredients to be contained in the pharmaceutical formulation of this invention may be selected as appropriate from a wide range with no limitations, but generally from about 1 to 70 wt %, preferably about 5 to 50 wt %.

Dosage regimen for the pharmaceutical formulation of this invention may be selected with no limitations, in the light of its dosage form; age, sex and other conditions of the patient; and severity of the disorder; for example, tablets, pills, solutions, suspensions, emulsions, granules and capsules may be orally administered; injections may be intravenously administered solely or in combination with common replacing fluid such as glucose solution and amino acid solution, or if necessary, administered intramuscularly, subcutaneously or intraperitoneally; and suppositories may be intrarectally administered.

Dosage of the pharmaceutical formulation of this invention may be selected as appropriate, in the light of its dosage regimen; age, sex and other conditions of the patient; and severity of the disorder. Preferably, the daily amount of the active ingredients may be about 0.0001 to 50 mg/kg. Preferably, a unit dosage form may contain about 0.001 to 1000 mg of the active ingredients.

The compounds of this invention have indicated no serious side effects or death within their effective dosage range in pharmacological studies.

EXAMPLES

Examples of preparation, formulation and evaluation for the compounds of this invention will be described, but this invention is not limited to the specific embodiments.

Preparation Example 1

Preparation of 1-(4-chlorophenyl)-3-(4-(2-methoxyethyl)piperazin-1-yl)methyl-2-pyrrolidinone (Table 1; Compound No. 146; racemic modification)

(1) Preparation of 1-(4-chlorophenyl)-2-pyrrolidinone

To a mixture of 372 g of p-chloroaniline and 251 g of γ-butyrolactone was added 75 mL of hydrochloric acid. The mixture was slowly warmed to an inner temperature of 110 to 115° C., and refluxed for 9 hours. Then, removing the refluxing liquid to slowly raise the inner temperature to 140° C., the reaction was continued for 8 hours. Consequently, 80 mL of the refluxing liquid was removed. After cooling to an inner temperature of 70° C., the mixture was dissolved in 2000 mL of ethyl acetate and washed sequentially with water, aqueous sodium carbonate solution and water. The organic layer was dried over magnesium sulfate and concentrated to about 1000 mL, and the precipitated crystals were collected by filtration. The filtrate was further concentrated to about 200 mL to collect the precipitated crystals. The combined crystals were washed with ethyl acetate and dried in vacuo to give 347 g of the title compound.

$^1$H NMR(CDCl$_3$, δ ppm): 2.17(2H, quintet), 2.61(2H, t), 3.83(2H, t), 7.32(2H, d), 7.58 (2H, d)

(2) Preparation of 1-(4-chlorophenyl)-3-ethoxycarbonyl-2-pyrrolidinone

To a suspension of 25 g of sodium hydride (60% oil dispersion) in 100 mL of tetrahydrofuran was added 37 g of diethyl carbonate. Under reflux, to the mixture was added dropwise a solution of 52.0 g of 1-(4-chlorophenyl)-2-pyrrolidinone in 150 mL of tetrahydrofuran over about 1.5 hours. After refluxing for 4.5 hours, the reaction mixture was cooled, and carefully poured into ice-water. The mixture was made to weakly alkaline with diluted hydrochloric acid and extracted with 300 mL of ethyl acetate. The organic layer was washed sequentially with water, aqueous sodium bicarbonate solution and water, dried over anhydrous magnesium sulfate and concentrated to give an oil. To the residue was added 200 mL of n-hexane, and the precipitated crystals were collected by filtration. The crystals were washed with n-hexane and dried in vacuo to give 60 g of the title compound.

$^1$H NMR (CDCl$_3$, δ ppm): 1.32(3H, t), 2.35–2.61(2H, m), 3.60–3.66(1H, m), 3.75–3.86(1H, m), 3.89–4.07(1H, m), 4.26(2H, q), 7.33(2H, d), 7.58(2H. d)

(3) Preparation of 1-(4-chlorophenyl)-3-hydroxymethyl-2-pyrrolidinone

Under ice-cooling, 3.9 g of sodium borohydride was added portionwise to a solution of 30.0 g of 1-(4-chlorophenyl)-3-ethoxycarbonyl-2-pyrrolidinone and 15 g of anhydrous calcium chloride in 150 mL of methanol. After completion of the reaction, the mixture was concentrated, and water and ethyl acetate were added. The mixture was acidified with diluted hydrochloric acid. After separation, the organic layer was washed with water, dried over anhydrous magnesium sulfate and concentrated. The residue was crystallized with n-hexane-ethyl ether. The crystals were collected by filtration, washed with a mixture of n-hexane and diethyl ether and dried in vacuo to give 23.3 g of the title compound.

$^1$H NMR(CDCl$_3$, δ ppm): 1.94–2.09(1H, m), 2.23–2.35 (1H, m), 2.83–2.94(1H, m), 2.99(1H, bs), 3.75–3.89(3H, m), 3.94–4.00(1H, m), 7.33(2H, dd), 7.59(2H, dd)

(4) Preparation of 1-(4-chlorophenyl)-3-mesyloxymethyl-2-pyrrolidinone

Under ice-cooling, 14.0 g of methanesulfonyl chloride was added dropwise to a solution of 23.2 g of 1-(4-chlorophenyl)-3-hydroxymethyl-2-pyrrolidinone and 12.5 g of triethylamine in 200 mL of dichloromethane. After 2 hours, the reaction mixture was washed with water, dried over anhydrous magnesium sulfate and concentrated to give crystals. The crystals were sludged with diethyl ether and collected by filtration. The crystals were washed with diethyl ether and dried in vacuo to give 29.8 g of the title compound.

$^1$H NMR(CDCl$_3$, δ ppm): 2.16–2.50(2H, m), 2.87–3.18 (4H, m), 3.77–3.87(2H, m), 4.43–4.67(2H, m), 7.34(2H, d), 7.58(2H, d)

(5) Preparation of 1-formyl-4-(2-methoxyethyl)piperazine

To a solution of 37.1 g of N-formylpiperazine and 37.1 g of anhydrous sodium carbonate in 50 mL of methanol was added dropwise 53.15 g of methoxyethyl bromide, and the mixture was refluxed for 3.5 hours. After cooling to room temperature, insolubles were filtered out and the filtrate was concentrated. To the residue was added water and chloroform. After separating the organic layer, the aqueous layer was extracted with chloroform. The combined organic layer was dried over anhydrous magnesium sulfate and concentrated to give 57.2 g of the title compound.

$^1$H NMR(CDCl$_3$, δ ppm): 2.45–2.54(4H, m), 2.59–2.63 (2H, m), 3.35–3.43(2H, m), 3.36(3H, s), 3.50–3.61(4H, m), 8.02(1H, s)

(6) Preparation of 1-(2-methoxyethyl)piperazine dihydrochloride

To a solution of 57.2 g of 1-formyl-4-methoxyethylpiperazine in 100 mL of methanol was added dropwise 180 mL of 4N-hydrochloric acid/1,4-dioxane over 1.5 hours. The mixture was stirred at room temperature for 1 hour, and the resulting crystals were filtered, washed with isopropyl ether and dried in vacuo to give 68.8 g of the title compound.

(7) Preparation of 1-(2-methoxyethyl)piperazine

To an aqueous solution of 68.8 g of 1-(2-methoxyethyl) piperazine dihydrochloride (water; 50 mL) was added dropwise an aqueous solution of 33.0 g of sodium hydroxide (water; 100 mL). The mixture was extracted with chloroform. The, organic layer was dried over anhydrous magnesium sulfate and evaporated to give 41.3 g of the title compound.

$^1$H NMR(CDCl$_3$, δ ppm): 1.80(1H, s), 2.47–2.60(6H, m), 2.90–2.94(4H, m), 3.36(3H, s), 3.52(2H, t)

(8) Preparation of 1-(4-chlorophenyl)-3-(4-(2-methoxyethyl)piperazin-1-yl)methyl-2-pyrrolidinone Triethylamine (8.0 g) was added to a solution of 18.5 g of 1-(4-chlorophenyl)-3-mesyloxymethyl-2-pyrrolidinone and 17.6 g of 1-(2-methoxyethyl)piperazine in 50 mL of acetonitrile, and the mixture was heated under reflux for 4 hours. After concentrating, water was added to the reaction mixture to precipitate crystals, which were then collected by filtration and dried in vacuo to give 18.5 g of the title compound.

Melting point: 103–105° C.; $^1$H NMR(CDCl$_3$, δ ppm): 2.01–2.12 (1H, m), 2.29–2.62 (12H, m), 2.78–2.94(2H, m), 3.35(3H, s), 3.51(2H, t), 3.74–3.80(2H, m), 7.32(2H, d), 7.59(2H, d)

Preparation Example 2

Preparation of 1-(4-chlorophenyl)-3-(4-(2-methoxyethyl)piperazin-1-yl)methyl-2-pyrrolidinone dihydrochloride(Table 2; Compound No. 50; racemic modification)

A solution of 1.41 g of 1-(4-chlorophenyl)-3-(4-(2-methoxyethyl)piperazin-1-yl)methyl-2-pyrrolidinone in 10 mL of methanol was acidified by adding 4N hydrochloric acid/1,4-dioxane. The precipitated crystals were collected by filtration, washed with diethyl ether and dried in vacuo to give 1.62 g of the title compound.

Melting point: 261–262° C.; $^1$H NMR(DMSO, δ ppm): 2.00–2.12(1H, m), 2.55(1H, m), 3.31(3H, s), 3.31–3.84 (17H, m), 7.46(2H, d), 7.72(2H, d)

Preparation Example 3

Preparation of 1-(4-chlorophenyl)-3-(4-(2-hydroxyethyl)piperazin-1-yl)methyl-2-pyrrolidinone (Table 1; Compound No. 145; racemic modification)

The title compound was prepared from 1-(4-chlorophenyl)-3-mesyloxymethyl-2-pyrrolidinone and 1-hydroxyethylpiperazine, in the same manner as in Preparation Example 1(8).

Melting point: 130–131° C.; $^1$H NMR(CDCl$_3$, δ ppm): 2.01–2.13(1H, m), 2.30–2.93(14H, m), 3.61(2H, t), 3.75–3.80(2H, m), 7.29–7.35(2H, m), 7.56–7.62(2H, m)

Preparation Example 4

Preparation of 1-(4-chlorophenyl)-3-(4-(2-hydroxyethyl)piperazin-1-yl)methyl-2-pyrrolidinone dihydrochloride(Table 2; Compound NO. 49; racemic modification)

The title compound was prepared in the same manner as in Preparation Example 2.

Melting point: 269.6–271.3° C.; $^1$H NMR(D$_2$O, δ ppm): 2.03–2.15(1H, m), 2.50–2.60(1H, m), 3.37–3.59(4H, m), 3.69–4.04(13H, m), 7.48(4H, s)

Preparation Example 5

Preparation of 1-(4-chlorophenyl)-3-(4-(3-hydroxypropyl)piperazin-1-yl)methyl-2-pyrrolidinone(Table 1; Compound No. 157; racemic modification)

(1) Preparation of 1-(3-hydroxypropyl)piperazine

The title compound was prepared from formylpiperazine and 3-bromo-1-propanol in the same manner as in Preparation Example 1(5) to (7).

$^1$H NMR(CDCl$_3$, δ ppm): 1.67–1.84(2H, m), 2.32–2.52 (2H, m), 2.59–2.67(4H, m), 2.88–2.94(4H, m), 3.77–3.82 (2H, (2) Preparation of 1-(4-chlorophenyl)-3-(4-(3-hydroxypropyl)piperazin-1-yl)methyl-2-pyrrolidinone The title compound was prepared from 1-(4-chlorophenyl)-3-mesyloxymethyl-2-pyrrolidinone and 1-hydroxypropylpiperazine, in the same manner as in Preparation Example 1(8).

$^1$H NMR(CDCl$_3$, δ ppm): 1.66–1.86(2H, m), 1.92–2.14 (1H, m), 2.29–2.41(1H, m), 2.43–2.66(11H, m), 2.76–2.96 (2H,m), 3.75–3.82(4H, m), 7.32(2H, d), 7.59(2H, d)

Preparation Example 6

Preparation of 1-(4-chlorophenyl)-3-(4-(3-hydroxypropyl)piperazin-1-yl)methyl-2-pyrrolidinone dihydrochloride(Table 2; Compound No 61; racemic modification)

The title compound was prepared in the same manner as in Preparation Example 2.

Melting point: 263.8–264.2° C.; $^1$H NMR(D$_2$O, δ ppm): 1.98–2.14(3H, m), 2.48–2.60(1H, m), 3.32–4.04(17H, m), 7.48(4H, s)

Preparation Example 7

Preparation of 1-(4-chlorophenyl)-3-(4-(2-ethoxyethyl)piperazin-1-yl)methyl-2-pyrrolidinone (Table 1; Compound No. 147; racemic modification)

(1) Preparation of 1-(2-ethoxyethyl)piperazine

The title compound was prepared from formylpiperazine and 2-bromoethyl ethyl ether in the same manner as in Preparation Example 1(5) to (7). $^1$H NMR(CDCl$_3$, δ ppm): 1.19(3H, t), 2.46–2.49(2H, m), 2.55–2.61(4H, m), 2.88–2.92 (4H, m), 3.45–3.59(4H, m)

(2) Preparation of 1-(4-chlorophenyl)-3-(4-(2-ethoxyethyl) piperazin-1-yl)methyl-2-pyrrolidinone The title compound was prepared from 1-(4-chlorophenyl)-3-mesyloxymethyl-2-pyrrolidinone and 1-ethoxyethylpiperazine, in the same manner as in Preparation Example 1(8).

$^1$H NMR(CDCl$_3$, δ ppm): 1.20(3H, t), 1.98–2.16(1H, m), 2.29–2.41(1H, m), 2.49–2.61(11H, m), 2.77–2.93(2H, m), 3.46–3.58(4H, m), 3.74–3.80(2H, m), 7.32(2H, d), 7.59(2H, d)

Preparation Example 8

Preparation of 1-(4-chlorophenyl)-3-(4-(2-ethoxyethyl)piperazin-1-yl)methyl-2-pyrrolidinone dihydrochloride(Table 2; Compound No. 51; racemic modification)

The title compound was prepared in the same manner as in Preparation Example 2.

Melting point: 261.0–261.4° C.; $^1$H NMR(D$_2$O, δ ppm): 1.21(3H, t), 1.99–2.15(1H, m), 2.50–2.61(1H, m), 3.34–3.46 (1H, m), 3.53–4.13(18H, m), 7.48(4H, s)

Preparation Example 9

Preparation of 1-(4-chlorophenyl)-3-(4-(2-(2-propynyloxy)ethyl)piperazin-1-yl)methyl-2-Pyrrolidinone(Table 1; Compound No. 156; racemic modification)

(1) Preparation of 1-tert-butoxycarbonyl-4-(2-hydroxyethyl) piperazine

To a solution of 10.00 g of 1-(2-hydroxyethyl)piperazine in 70 mL of dioxane at room temperature was added dropwise a solution of 16.43 g of di-tert-butyl dicarbonate in 30 mL of 1,4-dioxane with stirring. After completion of the reaction, the mixture was concentrated and n-hexane was added to the residue. The solid was collected by filtration and dried to give 14.11 g of the title compound.

(2) Preparation of 1-tert-butoxycarbonyl-4-(2-(2-propynyl) ethyl)piperazine

To a refluxing solution of 1.67 g of sodium hydride in 20 mL of tetrahydrofuran was added dropwise a solution of 9.00 g of 1-tert-butoxycarbonyl-4-(2-hydroxyethyl) piperazine in 15 mL of tetrahydrofuran and then 5.63 g of propargyl bromide was added dropwise to the resultant mixture. After completion of the reaction, the mixture was concentrated, poured into ice-water, and the mixture was extracted with ethyl acetate. The organic layer was dried over anhydrous magnesium sulfate and evaporated to give 10.70 g of the title compound.

(3) Preparation of 1-(2-(2-propynyloxy)ethyl)piperazine dihydrochloride

To a solution of 10.70 g of 1-tert-butoxycarbonyl-4-(2-(2-propynyl)ethyl)piperazine in 1,4-dioxane was added 4N hydrochloric acid/1,4-dioxane, and the mixture was stirred at 60° C. After completion of the reaction, the mixture was concentrated and diethyl ether was added. The solid was collected by filtration and dried to give 11.83 g of the title compound.

(4) Preparation of 1-(2-( 2-propynyloxy)ethyl)piperazine

To an aqueous solution of 11.83 g of 1-(2-(2-propynyloxy)ethyl)piperazine dihydrochloride (water: 10 mL) was added aqueous sodium hydroxide solution, and the mixture was extracted with ethyl acetate. The organic layer was dried over anhydrous magnesium sulfate and evaporated to give 3.09 g of the title compound.

$^1$H NMR(CDCl$_3$, δ ppm), 2.42(1H, t), 2.41–2.49(2H, m), 2.60(4H, t), 2.91(4H, t), 3.67(2H, t), 4.18(2H, d)

(5) Preparation of 1-(4-chlorophenyl)-3-(4-(2-(2-propynyloxy)ethyl)piperazin-1-yl)methyl-2-pyrrolidinone The title compound was prepared from 1-(4-chlorophenyl)-3-mesyloxymethyl-2-pyrrolidinone and 1-(2-(2-propynyloxy)ethyl)piperazine, in the same manner as in Preparation Example 1(8).

$^1$H NMR(CDCl$_3$, δ ppm): 1.94–2.12(1H, m), 2.29–2.39 (1H, m), 2.42(1H, t), 2.53–2.74(11H, m), 2.78–2.94(2H, m), 3.65–3.71(2H, m), 3.74–3.80(2H, m), 4.18(2H, d), 7.32(2H, d), 7.59(2H, d)

Preparation Example 10

Preparation of 1-(4-chlorophenyl)-3-(4-(2-(2-propynyloxy)ethyl)piperazin-1-yl)methyl-2-pyrrolidinonedihydrochloride(Table 2; Compound No.60; racemic modification)

The title compound was prepared in the same manner as in Preparation Example 2.

Melting point: 246.2–247.0° C.; $^1$H NMR(D$_2$O, δ ppm): 1.99–2.14(1H, m), 2.48–2.60(1H, m), 2.95(1H, t), 3.32–3.49 (1H, m), 3.51–4.23 (16H, m), 4.29(2H, d), 7.48(4H, s)

Preparation Example 11

Preparation of 1-(4-chlorophenyl)-3-(4-(3-methoxypropyl )piperazin-1-yl)methyl-2-pyrrolidinone(Table 1; Compound No. 158; racemic modification)

(1) Preparation of 1-(3-methoxypropyl)piperazine

The title compound was prepared from 1-piperazinepropanol in the same manner as in Preparation Example 9(1) to (4).

¹H NMR(CDCl₃, δ ppm): 1.72–1.82(2H, m), 2.37–2.43 (6H, m), 2.89(4H, t), 3.33(3H, s), 3.42(2H, t)

(2) Preparation of 1-(4-chlorophenyl)-3-(4-(3-methoxypropyl)piperazin-1-yl)methyl-2-pyrrolidinone The title compound was prepared from 1-(4-chlorophenyl)-3-mesyloxymethyl-2-pyrrolidinone and 1-(3-methoxypropyl)piperazine, in the same manner as in Preparation Example 1(8).

¹H NMR(CDCl₃, δ ppm): 1.71–1.82(2H, m), 2.01–2.12 (1H, m), 2.29–2.73(12H, m) 2.78–2.93(2H, m), 3.33(3H, s), 3.42(2H, t), 3.74–3.82(2H, m), 7.32(2H, d), 7.59(2H, d)

Preparation Example 12

Preparation of 1-(4-chlorophenyl)-3-(4-(3-methoxypropyl)piperazin-1-yl)methyl-2-pyrrolidinone dihydrochloride(Table 2; Compound No. 62; racemic modification)

The title compound was prepared in the same manner as in Preparation Example 2.

Melting point: 264.1–265.0° C.; ¹H NMR(D₂O, δ ppm): 2.02–2.14(3H, m), 2.49–2.60(1H, m), 3.37(3H, s), 3.32–4.04(17H, m), 7.48(4H, s)

Preparation Example 13

Preparation of 1-(3-chlorophenyl)-3-(4-(2-methoxyethyl)piperazin-1-yl)methyl-2-pyrrolidinone (Table 1; Compound No. 122; racemic modification)

(1) Preparation of 1-(3-chlorophenyl)-3-mesyloxymethyl-2-pyrrolidinone

The title compound was prepared from m-chloroaniline and γ-butyrolactone in the same manner as in Preparation Example 1(1) to (4).

¹H NMR(CDCl₃, δ ppm): 2.17–2.32(1H, m), 2.36–2.48 (1H, m), 2.99–3.08(1H, m), 3.06(3H, s), 3.82–3.87(2H, m), 4.48–4.52(1H, m), 4.58–4.63(1H, m), 7.10–7.13(1H, m), 7.20–7.34(1H, m), 7.50–7.54(1H, m), 7.69–7.70(1H, m)

(2) Preparation of 1-(3-chlorophenyl)-3-(4-(2-methoxyethyl)piperazin-1-yl)methyl-2-pyrrolidinone The title compound was prepared from 1-(3-chlorophenyl)-3-mesyloxymethyl-2-pyrrolidinone and 1-(2-methoxyethyl)piperazine, in the same manner as in Preparation Example 1(8).

¹H NMR(CDCl₃, δ ppm): 1.98–2.25(1H, m), 2.30–2.42 (1H, m), 2.53–2.65(11H, m), 2.78–2.94(2H, m), 3.35(3H, s), 3.49–3.54(2H, m), 3.71–3.84(2H, m), 7.10–7.13(1H, m), 7.25–7.31(1H, m), 7.54–7.58(1H, m), 7.67–7.69(1H, m)

Preparation Example 14

Preparation of 1-(3-chlorophenyl)-3-(4-(2-methoxyethyl)piperazin-1-yl)methyl-2-pyrrolidinone dihydrochloride(Table 2; Compound No. 2; racemic modification)

The title compound was prepared in the same manner as in Preparation Example 2.

Melting point: 227.6–228.1° C.; ¹H NMR(D₂O, δ ppm): 2.02–2.14(1H, m), 2.49–2.60(1H, m), 3.33–3.46(1H, m), 3.42(3H, s), 3.49–3.57(3H, m), 3.67–4.04(13H, m), 7.32–7.38(1H, m), 7.41–7.48(2H, m), 7.61(1H, s)

Preparation Example 15

Preparation of 1-(4-bromophenyl)-3-(4-(2-methoxyethyl)piperazin-1-yl)methyl-2-pyrrolidinone (Table 1; Compound No. 218; racemic modification)

(1) Preparation of 1-(4-bromophenyl)-3-mesyloxymethyl-2-pyrrolidinone

The title compound was prepared from p-bromoaniline and γ-butyrolactone in the same manner as in Preparation Example 1(1) to (4).

Melting point: 120–123° C.

(2) Preparation of 1-(4-bromophenyl)-3-(4-(2-methoxyethyl)piperazin-1-yl)methyl-2-pyrrolidinone The title compound was prepared from 1-(4-bromophenyl)-3-mesyloxymethyl-2-pyrrolidinone and 1-(2-methoxyethyl)piperazine, in the same manner as in Preparation Example 1(8).

¹H NMR(CDCl₃, δ ppm): 1.98–2.12(1H, m), 2.29–2.41 (1H, m), 2.53–2.63(11H, m), 2.78–2.94(2H, m), 3.35(3H, s), 3.51(2H, t), 3.74–3.82(2H, m), 7.46(2H, d), 7.54(2H, d)

Preparation Example 16

Preparation of 1-(4-bromophenyl)-3-(4-(2-methoxyethyl)piperazin-1-yl)methyl-2-pyrrolidinone dihydrochloride(Table 2; Compound No. 146; racemic modification)

The title compound was prepared in the same manner as in Preparation Example 2.

Melting point: 272.1–272.6° C.; ¹H NMR(DMSO, δ ppm): 1.99–2.07(1H, m), 3.05–3.84(18H, m), 3.31(3H, s), 7.58(2H, d), 7.66(2H, d)

Preparation Example 17

Preparation of 1-(3-bromophenyl)-3-(4-(2-methoxyethyl)piperazin-1-yl)methyl- 2-pyrrolidinone(Table 1; Compound No. 194; racemic modification)

(1) Preparation of 1-(3-bromophenyl)-3-mesyloxymethyl-2-pyrrolidinone

The title compound was prepared from m-bromoaniline and γ-butyrolactone in the same manner as in Preparation Example 1(1) to (4).

¹H NMR(CDCl₃, δ ppm): 2.21–2.39(1H, m), 2.41–2.48 (1H, m), 2.83–3.06(1H, m), 3.07(3H, s), 3.82–3.87(2H, m), 4.48–4.53(1H, m), 4.58–4.64(1H, m), 7.22–7.33(2H, m), 7.57–7.61(1H, m), 7.82–7.84(1H, m)

(2) Preparation of 1-(3-bromophenyl)-3-(4-(2-methoxyethyl)piperazin-1-yl)methyl-2-pyrrolidinone The title compound was prepared from 1-(3-bromophenyl)-3-mesyloxymethyl-2-pyrrolidinone and 1-(2-methoxyethyl)piperazine, in the same manner as in Preparation Example 1(8).

¹H NMR(CDCl₃, δ ppm): 2.01–2.12(1H, m), 2.34–2.60 (12H, m), 2.78–2.94(2H, m), 3.35(3H, s), 3.48–3.53(2H, m), 3.74–3.80(2H, m), 7.19–7.28(2H, m), 7.59–7.64(1H, m), 7.81(1H, d)

Preparation Example 18

Preparation of 1-(3-bromophenyl)-3-(4-(2-methoxyethyl)piperazin-1-yl)methyl-2-pyrrolidinone dihydrochloride(Table 2; Compound No. 98; racemic modification)

The title compound was prepared in the same manner as in Preparation Example 2.

Melting point: 237.8–238.8° C.; ¹H NMR(DMSO, δ ppm): 2.04(1H, m), 3.31(3H, s), 3.31–3.86(18H, m), 7.36–7.37(2H, m), 7.60–7.62(1H, m), 8.00(1H, s)

Preparation Example 19

Preparation of (R)-1-(4-chlorophenyl)-3-(4-(2-methoxyethyl)piperazin-1-yl)methyl-2-pyrrolidinone (R)-(−)-mandelate (Table 3; Compound No. 148; (R)-isomer)

To a hot solution of 66.6 g of 1-(4-chlorophenyl)-3-(4-(2-methoxyethyl)piperazin-1-yl)methyl-2-pyrrolidinone in 350 mL of ethyl acetate was added a hot solution of (R)-(−)-mandelic acid in 120 mL of ethyl acetate. After cooling, the precipitated crystals were filtered, washed with ethyl acetate and dried in vacuo to give 36.4 g of the title compound.

Melting point: 137–138° C.;

Enantiomer excess: at least 99% ee(calculated from the HPLC area ratio)

The enantiomer excess was calculated from the peak areas determined by liquid chromatography using a chiral column. The values hereinafter were determined in a similar manner.

$^1$H NMR(DMSO, δ ppm): 1.83–1.97(1H, m), 2.19–2.97 (14H, m), 3.23(3H, s), 3.41–3.48(2H, m), 3.70–3.81(2H, m), 4.94(1H, s), 7.21–7.38(5H, m), 7.41(2H, d). 7.69(2H, d)

Preparation Example 20

Preparation of (R)-1-(4-chlorophenyl)-3-(4-(2-methoxyethyl)piperazin-1-yl)methyl-2-pyrrolidinone (Table 1; Compound No. 146: (R)-isomer)

(R)-1-(4-chlorophenyl)-3-(4-(2-methoxyethyl)piperazin-1-yl)methyl-2-pyrrolidinone (R)-(−)-mandelate (30.5 g) recrystallized from 100 mL of ethanol was dissolved in 300 mL of water, and the solution was desalted with sodium carbonate and extracted with ethyl acetate. The organic layer was dried over anhydrous magnesium sulfate and concentrated to give 19.5 g of the title compound.

Melting point: 102–103° C.; Optical rotation:+; Enantiomer excess: at least 99% ee; $^1$H NMR(CDCl$_3$, δ ppm): 2.04(1H, m), 2.35(1H, m), 2.4–2.7(11H, m), 2.81(1H, m), 2.91(1H, dd), 3.35(3H, s), 3.51(2H, t), 3.77(2H, m), 7.32 (2H, d), 7.59(2H, d)

The title compound could be also synthesized by the following procedure:

A solution of L-tartaric acid (150 mg) in ethanol (1.5 ml) was added to 1-(4-chlorophenyl)-3-(4-(2-methoxyethyl) piperazin-1-yl)methyl-2-pyrrolidinone (351 mg) in ethanol (6 ml). The solid material thus precipitated was collected and subjected to desalting in an aqueous solution of sodium carbonate to obtain the title compound.

Enantiomer exess: 25% ee

Preparation Example 21

Preparation of (R)-1-(4-chlorophenyl)-3-(4-(2-methoxyethyl)piperazin-1-yl)methyl-2-pyrrolidinone dihydrochloride(Table 2; Compound No. 50; (R)-isomer)

A solution of 18.7 g of (R)-1-(4-chlorophenyl)-3-(4-(2-methoxyethyl)piperazin-1-yl)methyl-2-pyrrolidinone in 130 mL of methanol was acidified with 4N hydrochloric acid/ 1,4-dioxane. The precipitated crystals were filtered, washed with diethyl ether and dried in vacuo to give 22.6 g of the title compound.

Melting point: 252–253° C. (decomposed); Optical rotation:−; Enantiomer excess: at least 99% ee; $^1$H NMR (D$_2$O, δ ppm): 2.06(1H, m), 2.52(1H, m), 3.41(3H, s), 3.32–4.03(17H, m), 7.48(4H, s)

Preparation Example 22

Preparation of (S)-1-(4-chlorophenyl)-3-(4-(2-methoxyethyl)piperazin-1-yl)methyl-2-pyrrolidinone (S)-(+)-mandelate(Table 3; Compound No. 156; (S)-isomer)

Under heating, 152 mg of (S)-(+)-mandelic acid was added to a solution of 352 mg of 1-(4-chlorophenyl)-3-(4-(2-methoxyethyl)piperazin-1-yl)methyl-2-pyrrolidinone in 3 mL of ethyl acetate. After cooling, the precipitated crystals were filtered and dried in vacuo to give 180 mg of the title compound.

$^1$H NMR (DMSO, δ ppm): 1.83–1.97(1H, m), 2.19–2.97 (14H, m), 3.23(3H, s), 3.41–3.48(2H, m), 3.70–3.81(2H, m), 4.94(1H, s), 7.21–7.38(5H, m), 7.41(2H, d), 7.69(2H, d)

Preparation Example 23

Preparation of (S)-1-(4-chlorophenyl)-3-(4-(2-methoxyethyl)piperazin-1-yl)methyl-2-pyrrolidinone (Table 1; Compound No. 146; (S)-isomer)

Into 2 mL of water was dissolved 180 mg of (S)-1-(4-chlorophenyl)-3-(4-(2-methoxyethyl)piperazin-1-yl) methyl-2-pyrrolidinone (S)-(+)-mandelate, and the solution was desalted with sodium carbonate and extracted with ethyl acetate. The organic layer was dried over anhydrous magnesium sulfate and concentrated to give 120 mg of the title compound.

Melting point: 105–106° C.; Optical rotation:−; Enantiomer excess: at least 92% ee; $^1$H NMR(CDCl$_3$, δ ppm): 2.01–2.12(1H, m), 2.30–2.63(12H, m), 2;78–2.94(2H, m), 3.35(3H, s), 3.51(2H, t), 3.74–3.80(2H, m), 7.30–7.35(2H, m), 7.56–7.62(2H, m)

Preparation Example 24

Preparation of (S)-1-(4-chlorophenyl)-3-(4-(2-methoxyethyl)piperazin-1-yl)methyl-2-pyrrolidinone dihydrochloride(Table 2; Compound No. 50; (S)-isomer)

A solution of 1.0 g of (S)-1-(4-chlorophenyl)-3-(4-(2-methoxyethyl)piperazin-1-yl)methyl-2-pyrrolidinone in 50 mL of ethanol was acidified with 4N hydrochloric acid/1, 4-dioxane. The precipitated crystals were filtered, washed with diethyl ether and dried in vacuo to give 1.18 g of the title compound.

Melting point: 258° C. (decomposed); Optical rotation:+; Enantiomer excess: at least 99% ee; $^1$H NMR(D$_2$O, δ ppm): 2.06(1H, m), 2.52(1H, m), 3.41(3H, s), 3.32–4.03(17H, m), 7.48(4H, s)

Preparation Example 25

Preparation of (R)-1-(4-chlorophenyl)-3-(4-(2-methoxyethyl)piperazin-1-yl)methyl-2-pyrrolidinone dihydrochloride dihydrate(Table 2; Compound No. 74; (R)-isomer)

(R)-1-(4-chlorophenyl)-3-(4-(2-methoxyethyl)piperazin-1-yl)methyl-2-pyrrolidinone dihydrochloride (1.98 g) was placed in an incubator kept at 25° C. under a relative humidity of 75% for 24 hours to give 2.14 g of the title compound.

Melting point: 264.6–265.1° C. (decomposed) Optical rotation:−; Enantiomer excess: at least 99% ee; $^1$H NMR (D$_2$O, δ ppm): 2.06(1H, m), 2.52(1H, m), 3.41(3H, s), 3.32–4.03(17H, m), 7.48(4H, s)

Alternatively, the compound may be prepared as follows.

Under reflux, water was added dropwise to a suspension of 100 mg of (R)-1-(4-chlorophenyl)-3-(4-(2-methoxyethyl) piperazin-1-yl)methyl-2-pyrrolidinone dihydrochloride in 3 mL of ethanol until the reaction system became homogeneous. After cooling to room temperature, the precipitated solid was filtered and dried to give 88.5 mg of the title compound.

Preparation Example 26

Preparation of (R)-1-(4-chlorophenyl)-3-(4-(2-methoxyethyl)piperazin-1-yl)methyl-2-pyrrolidinone dihydrobromide(Table 3; Compound No. 11; (R)-isomer)

To a mixture of 379 mg of 47% hydrobromic acid aq. and 10 mL of ethanol was added a solution of 352 mg of (R)-1-(4-chlorophenyl)-3-(4-(2-methoxyethyl)piperazin-1-yl)methyl-2-pyrrolidinone in 10 mL of ethanol. The mixture was stirred at room temperature and then cooled. The precipitated solid was filtered and dried to give 488 mg of the title compound.

Melting point: 244.1–245.1° C.; $^1$H NMR(DMSO, δ ppm): 1.90–2.60(1H, m), 2.40–2.55(1H, m,2.78–4.00(20H, m), 7.46(2H, d), 7.73(2H, d)

Preparation Example 27

Preparation of (R)-1-(4-chlorophenyl)-3-(4-(2-methoxyethyl)piperazin-1-yl)methyl-2-pyrrolidinone sulfate monohydrate(Table 3; Compound No. 32; (R)-isomer)

A solution of 101 mg of conc. sulfuric acid in 5 mL of ethanol was added to a solution of 352 mg of (R)-1-(4-chlorophenyl)-3-(4-(2-methoxyethyl)piperazin-1-yl)methyl-2-pyrrolidinone in 10 mL of ethanol. The mixture was stirred at room temperature and then concentrated to 3 mL. To the mixture was added 5 mL of ethyl acetate. The precipitated solid was filtered and dried to give 389 mg of the title compound.

Melting point: 166.4–166.7° C.; $^1$H NMR (DMSO, δ ppm): 1.84–1.99(1H, m), 2.15–4.35(21H, m), 7.44(2H, d), 7.71(2H, d)

Preparation Example 28

Preparation of (R)-1-(4-chlorophenyl)-3-(4-(2-methoxyethyl)piperazin-1-yl)methyl-2-pyrrolidinone benzenesulfonate monohydrate(Table 3; Compound No.132; (R)-isomer)

To a solution of 176 mg of benzenesulfonic acid monohydrate in 10 mL of ethanol was added a solution of 352 mg of (R)-1-(4-chlorophenyl)-3-(4-( 2-methoxyethyl)piperazin-1-yl)methyl-2-pyrrolidinone in 10 mL of ethanol. The mixture was concentrated. The residue was sludged with ethanol. The solid formed was filtered and dried to give 407 mg of the title compound.

Melting point: 82.2–85.9° C.; $^1$H NMR (DMSO, δ ppm): 1.88–1.99(1H, m), 2.31–3.81(21H, m), 7.31–7.36(3H, m), 7.43(2H, d), 7.59–7.68(2H, m), 7.69–7.72(2H, m)

Preparation Example 29

Preparation of (R)-1-(4-chlorophenyl)-3-(4-(2-methoxyethyl)piperazin-1-yl)methyl-2-pyrrolidinone dibenzenesulfonate 3.5 hydrate(Table 3; Compound No. 139; (R)-isomer)

To a solution of 352 mg of benzenesulfonic acid monohydrate in 10 mL of ethyl acetate was added a solution of 352 mg of (R)-1-(4-chlorophenyl)-3-(4-(2-methoxyethyl)piperazin-1-yl)methyl-2-pyrrolidinone in 10 mL of ethyl acetate. The mixture was stirred at room temperature and cooled. The precipitated solid was filtered and dried to give 585 mg of the title compound.

Melting point: 162.5–163.4° C.; $^1$H NMR(DMSO, δ ppm): 1.78–1.97(1H, m), 2.18–3.84(21H, m), 7.23–7.36 (6H, m), 7.45–7.49(2H, m), 7.58–7.64(4H, m), 7.70–7.75 (2H, m)

Preparation Example 30

Preparation of (R)-1-(4-chlorophenyl)-3-(4-( 2-methoxyethyl)piperazin-1-yl)methyl-2-pyrrolidinone di-p-toluenesulfonate dihydrate(Table 2; Compound No. 129; (R)-isomer)

To a solution of 380 mg of p-toluenesulfonic acid monohydrate in 10 mL of ethyl acetate was added a solution of 352 mg of (R)-1-(4-chlorophenyl)-3-(4-(2-methoxyethyl)piperazin-1-yl)methyl-2-pyrrolidinone in 10 mL of ethyl acetate. The mixture was stirred at room temperature and cooled. The precipitated solid was filtered and dried to give 712 mg of the title compound.

Melting point: 209.8–210.3° C.; $^1$H NMR(DMSO, δ ppm): 1.85–2.10(1H, m), 2.25–2.50(1H, m), 2.29 (6H, s), 2.70–3.95 (20H, m), 7.12 (4H, d), 7.30(2H, d), 7.45–7.49 (6H, m)

Preparation Example 31

Preparation of (R)-1-(4-chlorophenyl)-3-(4-(2-methoxyethyl)piperazin-1-yl)methyl-2-pyrrolidinone methanesulfonate(Table 3; Compound No. 107; (R)-isomer)

A solution of 240 mg of methanesulfonic acid in 5 mL of ethyl acetate was added to a solution of 880 mg of (R)-1-(4-chlorophenyl)-3-(4-(2-methoxyethyl)piperazin-1-yl)methyl-2-pyrrolidinone in 15 mL of ethyl acetate. The mixture was stirred at room temperature and cooled. The precipitated solid was filtered and dried to give 892 mg of the title compound.

$^1$H NMR(D$_2$O, δ ppm): 1.95–2.10(1H, s), 2.41–2.55(1H, s), 2.74–3.45(13H, m), 2.80(3H, s), 3.39(3H, s), 3.73–3.77 (2H, m), 3.81–3.97(2H, m), 7.46(4H, s)

Preparation Example 32

Preparation of (R)-1-(4-chlorophenyl)-3-(4-(2-methoxyethyl)piperazin-1-yl)methyl-2-pyrrolidinone dimethanesulfonate(Table 3; Compound No. 111; (R)-isomer)

A solution of 480 mg of methanesulfonic acid in 5 mL of ethyl acetate was added to a solution of 880 mg of (R)-1-(4-chlorophenyl)-3-(4-(2-methoxyethyl)piperazin-1-yl)methyl-2-pyrrolidinone in 15 mL of ethyl acetate. The mixture was stirred at room temperature and cooled. The precipitated solid was filtered and dried to give 1127 mg of the title compound.

$^1$H NMR(D$_2$O, δ ppm): 1.98–2.13(1H, m), 2.49–2.62(1H, m), 2.80(6H, s), 3.31–4.19(17H, m), 3.41(3H, s), 7.48(4H, s)

Preparation Example 33

Preparation of (R)-1-(4-chlorophenyl)-3-(4-(2-methoxyethyl)piperazin-1-yl)methyl-2-pyrrolidinone L-lactate(Table 3; Compound No. 140; (R)-isomer)

A mixture of 106 mg of 85% L-lactic acid aq. and 10 mL of ethyl acetate was added to a solution of 352 mg of (R)-1-(4-chlorophenyl)-3-(4-(2-methoxyethyl)piperazin-1-yl)methyl-2-pyrrolidinone in 10 mL of ethyl acetate. The mixture was stirred at room temperature and then concentrated. The residue was sludged with diethyl ether and dried to give 180 mg of the title compound.

$^1$H NMR(DMSO, δ ppm): 1.23(3H, d), 1.80–2.00(1H, m), 2.15–4.10(23H, m), 7.43(2H, d), 7.70(2H, d)

Preparation Example 34

Preparation of (R)-1-(4-chlorophenyl)-3-(4-(2-methoxyethyl)piperazin-1-yl)methyl-2-pyrrolidinone L-tartrate(Table 3; Compound No. 180; (R)-isomer)

To a solution of 150 mg of L-tartaric acid in 10 mL of ethanol was added a solution of 352 mg of (R)-1-(4-chlorophenyl)-3-(4-(2-methoxyethyl)piperazin-1-yl)methyl-2-pyrrolidinone in 10 mL of ethyl acetate. The mixture was stirred at room temperature and cooled. The precipitated solid was filtered and dried to give 488 mg of the title compound.

Melting point: 183.2–184.9° C.; $^1$H NMR(DMSO, δ ppm): 1.82–1.94(1H, m), 2.21–3.79(21H, m), 4.17(2H, s), 7.40–7.46(2H, m), 7.67–7.73(2H, m)

Alternatively, the compound may be prepared as follows.

Into 62 mL of 18% water-ethanol were suspended 5.00 g of (R)-1-(4-chlorophenyl)-3-(4-(2-methoxyethyl)piperazin-1-yl)methyl-2-pyrrolidinone and 2.13 g of L-tartaric acid. After making it homogeneous by heating under reflux, the solution was cooled. The precipitated solid was filtered and dried to give 6.39 g of the title compound.

Preparation Example 35

Preparation of (R)-1-(4-chlorophenyl)-3-(4-(2methoxyethyl)piperazin-1-yl)methyl-2-pyrrolidinone di-L-tartrate dihydrate(Table 3; Compound No. 186; (R)-isomer)

To a solution of 300 mg of L-tartaric acid in 20 mL of ethanol was added a solution of 352 mg of (R)-1-(4-chlorophenyl)-3-(4-(2-methoxyethyl)piperazin-1-yl)methyl-2-pyrrolidinone in 10 mL of ethanol. The mixture was stirred at room temperature and cooled. The precipitated solid was filtered and dried to give 205 mg of the title compound.

$^1$H NMR(DMSO, δ ppm): 1.87–1.98 (1H, m), 2.25–2.89 (14H, m), 3.25(3H, s), 3.41–3.51(2H, m), 3.74–3.80(2H, m), 4.21(4H, s), 7.42(2H, dd), 7.70(2H, dd)

Preparation Example 36

Preparation of (R)-1-(4-chlorophenyl)-3-(4-(2-methoxyethyl)piperazin-1-yl)methyl-2-pyrrolidinone di-D-tartrate(Table 3; Compound No. 192; (R)-isomer)

A solution of 75 mg of D-tartaric acid in 3 mL of ethanol was added to a solution of 176 mg of (R)-1-(4-chlorophenyl)-3-(4-(2-methoxyethyl)piperazin-1-yl)methyl-2-pyrrolidinone in 3 mL of ethanol. The mixture was stirred at room temperature and cooled. The precipitated solid was filtered and dried to give 110 mg of the title compound.

$^1$H NMR(DMSO, δ ppm): 1.86–1.94(1H, m), 2.25–3.00 (14H, m), 3.25(3H, s), 3.47–3.51(2H, m), 3.74–3.80(2H, m), 4.22(2H, s), 7.43(2H, d), 7.70(2H, d)

The title compound could be also synthesized by the following procedure:

A solution of D-tartaric acid (450 mg) in ethanol (6 ml) was added dropwise at an outer temperature between 50 and 60° C. to a solution of 1-(4-chlorophenyl)-3-(4-(2-methoxyethyl)piperazin-1-yl)methyl-2-pyrrolidinone (1056mg) in ethanol (6ml). The reaction mixture was allowed to stand for cooling and the solid material thus precipitated was collected by filtration. The solid material was further crystallized in 10 ml of ethanol to obtain 372 mg of the title compound. Enantiomer excess: 97% ee Preparation Example 37

Preparation of (R)-1-(4-chlorophenyl)-3-(4-(2-methoxyethyl)piperazin-1-yl)methyl-2-pyrrolidinone disuccinate(Table 3; Compound No. 75; (R)-isomer)

A solution of 591 mg of succinic acid in 20 mL of ethanol was added to a solution of 880 mg of (R)-1-(4-chlorophenyl)-3-(4-(2-methoxyethyl)piperazin-1-yl)methyl-2-pyrrolidinone in 20 mL of ethanol. The mixture was stirred at room temperature and cooled. The precipitated solid was filtered and dried to give 356 mg of the title compound.

Melting point: 98.1–99.1° C.; $^1$H NMR(DMSO, δ ppm): 1.82–1.96(1H, m), 2.18–2.97(14H, m), 2.41(4H, s), 3.23 (3H, s), 3.41–3.45(2H, m), 3.70–3.81(2H, m), 7.43(2H, d), 7.70(2H, d)

Preparation Example 38

Preparation of (R)-1-(4-chlorophenyl)-3-(4-(2-methoxyethyl)piperazin-1-yl)methyl-2-pyrrolidinone difumarate(Table 3; Compound No. 59; (R)-isomer)

Into 62 mL of 13% water-ethanol were suspended 5.00 g of (R)-1-(4-chlorophenyl)-3-(4-(2-methoxyethyl)piperazin-1-yl)methyl-2-pyrrolidinone and 3.30 g of fumaric acid. After making it homogeneous by heating under reflux, the solution was cooled. The precipitated solid was filtered and dried to give 7.45 g of the title compound.

Melting point: 192–193° C.; $^1$H NMR(DMSO, δ ppm): 1.82–1.97(1H, m), 2.19–2.31(1H, m), 2.35–2.97(13H, m), 3.24(31H, s), 3.44–3.48 (2H, m), 3.73–3.79(2H, m), 6.60 (4H, s), 7.43(2H, d), 7.70(2H, d)

Preparation Example 39

Preparation of (R)-1-(4-chlorophenyl)-3-(4-(2-methoxyethyl)piperazin-1-yl)methyl-2-pyrrolidinone dimaleate(Table 3; Compound No. 67; (R)-isomer)

Into 62 mL of 9% water-ethanol were suspended 5.00 g of (R)-1-(4-chlorophenyl)-3-(4-(2-methoxyethyl)piperazin-1-yl)methyl-2-pyrrolidinone and 3.30 g of maleic acid. After making it homogeneous by heating under reflux, the solution was cooled. The precipitated solid was filtered and dried to give 7.10 g of the title compound.

Melting point: 178.5–179.1° C.; 1H NMR(DMSO, δ ppm): 1.76–1.98(1H, m), 2.23–2.35(1H, m), 2.66–3.30 (13H, m), 3.30(3H, s), 3.60–3.72(2H, m), 3.76–3.81(2H, m), 6.14(4H, s), 7.44(2H, d), 7.71(2H, d)

Formulation Example 1

Tablets were prepared using the following components.

(R)-1-(4-chlorophenyl)-3-[(4-(2-methoxyethyl)piperazin-1-yl)methyl]-2-pyrrolidinone hydrochloride (Table 2; Compound No. 50; (R)-isomer; produced in Preparation

| | |
|---|---|
| Example 21 | 120 g |
| Citric acid | 1 g |
| Lactose | 35 g |
| Calcium phosphate, dibasic | 72 g |
| Pluronic F-68 | 30 g |
| Sodium lauryl sulfate | 20 g |
| Polyvinylpyrrolidone | 14 g |
| Polyethylene glycol (Carbowax 1500) | 5 g |
| Polyethylene glycol (Carbowax 6000) | 45 g |
| Corn starch | 33 g |
| Dried sodium stearate | 3 g |
| Dried magnesium stearate | 3 g |
| Ethanol | quantum sufficiat |

First, the above pyrrolidinone derivative hydrochloride, citric acid, lactose, dibasic calcium phosphate, Pluronic F-68 and sodium lauryl sulfate were blended. The mixture was sieved with a No.60 screen and wet-granulated with an alcoholic solution containing polyvinylpyrrolidone, Carbowax 1500 and Carbowax 6000, during which alcohol was, when necessary, added to make the powder a paste mass. Corn starch was added to the resulting granules, and the mixture was blended until homogeneous granules were formed. The mixture was passed through a No.10 screen, placed on a tray, dried in an oven at 100° C. for 12 to 15 hours, and sieved with a No.16 screen. To the powder were added dried sodium lauryl sulfate, and the mixture was blended and compressed with a tablet machine to a desired form to give uncoated tablets.

The uncoated tablets were treated with varnish after spraying talc for prevention of moisture absorption, the tablets were coated with a primer layer (varnish-coating layer). The primer layer was formed by a sufficient number of application of varnish for oral administration. For rounding and smoothing the tablets, a further primer layer and a smooth coating were applied with varnish. Furthermore, coloring coating was applied until a desired coating was formed. After drying the coated tablets were polished to give evenly bright tablets.

Evaluation Example 1 (Radioreceptor assay for a $\sigma_1$ receptor)

Procedure

Radioreceptor assay for a $\sigma_1$ receptor was conducted according to a modified method of Vilner et al.(B. J. Vilner and W. D. Bowen, Multiple Sigma and PCP Receptor Ligands: Mechanisms for Neuromodulation and Neuroprotection?, NPP Books: pp.341(1992)). $P_2$ fraction (20 mg/mL) prepared from a whole brain of a guinea pig without cerebellum and medulla was incubated with a test drug and a $^3$H-ligand (3 nM $^3$H-(+)pentazocine(NEN)) at room temperature for 2 hours.

The brain tissue was vacuum-filtrated on a glass-fiber filter paper(Whatman, GF/B) with Cell Harvester(Brandel, LL-12), and then washed with buffer (3 mL×2). The glass-fiber filter paper was placed in a vial. Into the vial was added 3.5 mL of scintillator (Amersham, ACSII), and after 10 hours the amount of the $^3$H-ligand binding to the receptor was determined with a liquid scintillation counter. Blank was determined using (+)-pentazocine (10 $\mu$M).

Binding rates of the $^3$H-ligand to the receptor for various concentration of the test drug were plotted in a graph where a rate without the test drug=100% and a rate with the blank compound=0%, and the concentration of the test drug showing a binding rate of 50% was determined as $IC_{50}$. From the $IC_{50}$, Ki value was calculated according to the following equation:

$$Ki=IC_{50}/\{1+[^3H\text{-ligand}]/K_D\}$$

wherein $K_D$ is a dissociation constant between the $^3$H-ligand and the receptor calculated by Scatchard plotting for binding of the $^3$H-ligand to the receptor, changing the concentration of the $^3$H-ligand.

Rimcazole was also evaluated.

Results

The results are shown in Table 4, indicating that the compounds of this invention had high affinity for a $\sigma_1$ receptor.

Evaluation Example 2 (Radioreceptor assay for $D_2$ receptor)

Procedure $^3$H-spiperone (Amersham) and a test drug were incubated with a homogenate of rat cerebral striatal site as described in D. R. Burt et al., Proc.Natl.Acad.Sci.U.S.A. 72:4655 (1975), and Ki value was determined as described in the above r radioreceptor assay.

Rimcazole was also evaluated.

Results

The results are also shown in Table 4, indicating that the compounds of this invention did not have affinity for a $D_2$ receptor.

TABLE 4

| | Affinity for a receptor | |
|---|---|---|
| | Ki (nM) | |
| Preparation Example No. | $\sigma_1$ | $D_2$ |
| 2 | 85 | >3300 |
| 8 | 14 | >3300 |
| 10 | 10 | >3300 |
| 18 | 7.5 | >2800 |
| 21 | 72 | >3900 |
| Rimcazole | 1000 | 11600 |

Evaluation Example 3 (Anti-SKF effect)

Procedure

Antipsychotic activity for a test drug was studied by means of head weaving behavior induced by a $\sigma$-receptor agonist SKF-10047 for a mouse. For the experiment were used 10 male ddY mice aged 5 weeks (Nippon SLC) per a group. The mice were placed in a measuring cage and calmed 1 hour before the initiation of the test. To the mice was orally administered a test drug and after 60 min was subcutaneously administered SKF-10047 in a dose of 20 mg/kg. After 20 min, head weaving was counted for 10 min. Efficacy of the drug was evaluated by determining an inhibition (%) compared with the control group from the average of the 10 min scores of the test-drug groups, 20 min after administering SKF-10047, and then estimating a $ED_{50}$ value.

The compound represented by the following formula (IV) which is described in Japanese Patent Laid-Open (Kokai) No. 252219/95 (JP-A 7-252219) was also evaluated.

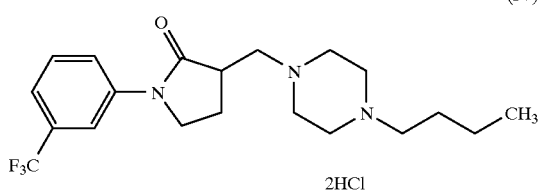

(IV)

Results

The results are shown in Table 5, indicating that the compounds of this invention had a higher antipsychotic activity than the compound of formula (IV).

Evaluation Example 4 (Anti-PCP effect)

Antipsychotic activity for a test drug was studied by means of head weaving behavior induced by phencyclidine (PCP) for a rat. For the experiment were used male Wistar (ST) rats aged 4weeks (Nippon SLC). The rats were placed in a measuring cage and calmed 1 hour before the initiation of the test. To the rats was orally administered a test drug and after 60 min was intraperitoneally administered PCP in a dose of 7.5 mg/kg. After 20 min, head weaving was counted for 10 min. Efficacy of the drug was evaluated by determining an inhibition (%) compared with the control group from the average of the scores of the test-drug groups, and then estimating a $ED_{50}$ value.

The compound of formula (IV) described in JP-A 7-252219 was also evaluated.

Results

The results are also shown in Table 5, indicating that the compounds of this invention had a higher antipsychotic activity than the compound of formula (IV).

TABLE 5

Antipsychotic activity

| Preparation Example No. | $ED_{50}$ (mg/kg) Oral treatment before 60 min | |
|---|---|---|
| | Anti-SKF | Anti-PCP |
| 2 | 2.1 | 1.3 |
| 16 | 0.52 | 1.9 |
| 21 | 0.77 | 0.75 |
| 37 | — | 1.15 |
| 38 | — | 1.48 |
| 39 | — | 1.08 |
| Compound of formula (IV) | 14 | 11 |

Evaluation Example 5 (Persistence of anti-SKF effect) Procedure

Persistence of antipsychotic activity for a test drug was studied by means of head weaving behavior induced by a receptor agonist SKF-10047 for a mouse. For the experiment were used 10 male ddY mice aged 5 weeks (Nippon SLC) per a group. The mice were placed in a measuring cage and calmed 1 hour before the initiation of the test. To the mice was orally administered a test drug and after 4 hours was subcutaneously administered SKF-10047 in a dose of 20 mg/kg. After 20 min, head weaving was counted for 10 min. Efficacy of the drug was evaluated by determining an inhibition (%) compared with the control group from the average of the 10 min scores of the test-drug groups, 20 min after administering of SKF-10047, and then estimating a $ED_{50}$ value.

The compound of formula (IV) described in JP-A 7-252219 and the compound represented by the following formula (V) which is described in Japanese Patent Laid-Open (Kokai) No. 40667/97 (JP-A 9-40667) were also evaluated.

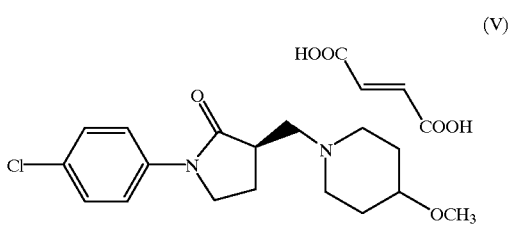

(V)

Results

The results are shown in Table 6, indicating that the compound of this invention was effective for more than 4 hours and improved in its duration of effectiveness compared with the compounds of the above formulas (IV) and (V).

TABLE 6

Persistence of anti-SKF effect

| Preparation Example No. | $ED_{50}$ (mg/kg) (after 4 hours) |
|---|---|
| 21 | 3.19 |
| Compd. of formula (IV) | >100 |
| Compd. of formula (V) | 23.2 |

Evaluation Example 6 (Effect to reverse tolerance development due to repetitive administration of methamphetamine)

Procedure

For the experiment, male Std:Wistar(ST) rat (Nippon SLC) aged 5 weeks were used. A test drug, the compound of formula (IV) described in JP-A 7-252219 or the compound of formula (V) described in JP-A 9-40667 was dissolved in purified water or 0.5% C.M.C./saline. Methamphetamine (mAMP) was dissolved in saline. Dosage volume was 1 mL/kg body weight.

Test Procedure a) Repetitive Administration of a Test Drug and mAMP

The drugs were repetitively administered for 10 days with a regimen that to a rat, a test drug was orally or intraperitoneally administered and after 60 min mAMP was intraperitoneally administered in a dose of 2 mg/kg. To a normal group, solvent alone was administered in place of the combination of the test drug and mAMP. To a control group, solvent was orally or intraperitoneally administered, and then intraperitoneally mAMP was additionally administered.

b) Effect of a Test Drug on a Process of Reverse Tolerance Development

After the repetitive administration, there was provided a withdrawal period for 7 days during which the test drug or mAMP was not administered. After the withdrawal, the test drug was discontinued and mAMP was administered in a dose of 2 mg/kg, and then stereotyped behavior of the animal was observed.

c) Rating of Stereotyped Behavior

After administering mAMP, stereotyped behavior was rated in accordance with the following scale, for 1 min every 10 min until 60 min.

Scale

0: Calm

1: Common behavior with exploratory activities

2: Sniffing and head-movement with hyperkinesis

3: Intermittent sniffing and head-movement with periodical hyperkinesis

4: Almost continuous sniffing and head-movement with occasional transposition movement 5: Continuous sniffing and head-movement without transposition movement The results are expressed as an inhibition (%) of reverse tolerance development calculated from the following equation, using a total score for six minutes: Inhibition of reverse tolerance development (%)=100−A wherein A represents a value calculated from the following equation:

$A=[\{(\text{Score for the test drug group})-(\text{Score for the normal group})\}/\{(\text{Score for the control group})-(\text{Score for the normal group})\}]\times 100$ Results The results are shown in Table 7, indicating that the compound of this invention dose-dependently inhibited reverse tolerance development to methamphetamine; specifically it almost completely inhibited reverse tolerance in a dose of 15 mg/kg (oral administration). In contrast, the cited compounds in an intraperitoneal dose of 30 mg/kg showed inhibition effect comparable to the compound of this invention, which indicates that the compound of this invention had significantly higher effect than the cited compounds.

TABLE 7

Effect on reverse tolerance development due to repetitive administration of methamphetamine

| Preparation Example No. | Dose (mg/kg) | Route of administration | Inhibition of reverse tolerance (%) |
|---|---|---|---|
| 21 | 7.5 | Oral | 81.0 |
| 21 | 15.0 | Oral | 93.9 |
| Compd. of formula IV | 30.0 | Intraperitoneal | 92.9 |
| Compd. of formula V | 10.0 | Intraperitoneal | 81.7 |
| Compd. of formula V | 30.0 | Intraperitoneal | 87.8 |

Evaluation Example 7 (Blood kinetics)

Procedure

For the experiment, male beagle dogs were employed. A test drug was intravenously or orally administered in a dose of 10 mg/kg. Blood samples were collected at 0.25, 0.5, 1, 2, 4, 6 and 24 hours after administering the test drug, and the samples were centrifuged to separate plasma, for which a plasma level of the test drug was determined by HPLC. Half-life of the test drug in blood was estimated from the results at the intravenous administration. An extent of bioavailability is expressed as a rate of AUC at the oral administration to AUC at the intravenous administration.

The compound of formula (V) described in JP-A 9-40667 was also evaluated.

Results

The results are shown in Table 8, indicating that the compound of this invention had a longer half-life and was significantly improved in an extent of bioavailability, compared with the compound of formula (V).

TABLE 8

Blood kinetics parameters

| Preparation Example No. | Half-life (hour) | $C_{MAX}$ (µg/mL) | Extent of Bioavailability (%) |
|---|---|---|---|
| 21 | 3.5 | 1.52 | 83.1 |
| Compd. of formula (V) | 1.5 | 0.46 | 64.3 |

Evaluation Example 8 (Safety)

Procedure

For the experiment, male Std:ddY mice aged 5 weeks were used. The mice were weighed, and then calmed in an observation cage for more than 1 hour. To the mice, a test drug was orally administered in a dose of 300 mg/kg to observe them for general symptoms until 2 hours.

The compounds of formulas (IV) and (V) described in JP-A 7-252219 and 9-40667, respectively, were also evaluated.

Results

The results are shown in Table 9, indicating that the compounds of this invention exhibited no toxicity, i.e., a significant reduction in toxicity compared with the compound of formula (IV).

TABLE 9

Simple acute toxicity for a mouse

| Preparation Example No. | Convulsion/Treatment | Death/Treatment |
|---|---|---|
| 2 | 0/6 | 0/6 |
| 8 | 0/3 | 0/3 |
| 16 | 0/5 | 0/5 |
| 21 | 0/4 | 0/4 |
| Compd. of formula (IV) | 5/5 | 5/5 |
| Compd. of formula (V) | 1/3 | 0/3 |

It was demonstrated that the compounds of this invention had affinity for a σ receptor and high antipsychotic activity, i.e., anti-SKF and anti-PCP effects. They were highly effective to a methamphetamine (mAMP)-induced reverse tolerance model, i.e., an exacerbation model of schizophrenia. Since they do not have affinity for a dopamine receptor and can inhibit reverse tolerance without extrapyramidal side effects, the compounds of this invention may be expected to be effective against recurrence or intractabilization of schizophrenia.

Furthermore, the compounds of this invention are highly selective toward a $\sigma_1$ receptor compared with a $\sigma_2$ receptor, and inhibited not only head weaving but also rearing, for PCP-induced abnormal behavior. Furthermore, the compounds of this invention surprisingly inhibited a dopaminergic activity, apomorphine-induced climbing behavior, in spite of no affinity for a dopamine receptor, while exhibiting no effect on apomorphine-induced stereotyped behavior (side effects).

Optically resolved compounds of this invention which were optically resolved from the racemic modifications exhibited more improved affinity for a σ receptor, and more improved antipsychotic activity.

The compounds of this invention showed significantly longer duration of drug efficacy and an improved extent of bioavailability than the cited compounds described in JP-A 7-252219 and JP-A 9-40667, respectively, and much higher effect in a metamphetamine (mAMP) reverse tolerance model than the cited compounds. Furthermore, the compounds of this invention were significantly improved in safety compared with the compound described in JP-A 7-252219.

What is claimed is:

1. A pyrrolidinone derivative represented by general formula (1) or a pharmaceutically acceptable salt thereof or a hydrate of the pharmaceutically acceptable salt:

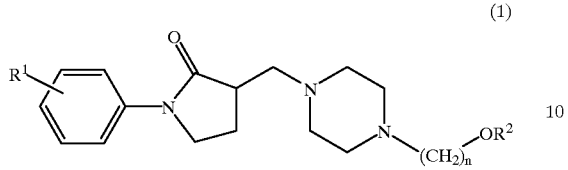

(1)

wherein $R^1$ is hydrogen or a halogen; $R^2$ is hydrogen, a $C_{1-3}$ alkyl, a $C_{2-3}$ alkenyl or a $C_{2-3}$ alkynyl; and n is an integer of 2 to 3.

2. A pyrrolidinone derivative or a pharmaceutically acceptable salt thereof or a hydrate of the pharmaceutically acceptable salt as claimed in claim 1, wherein $R^1$ is chlorine or bromine, $R^2$ is a $C_{1-3}$ alkyl, and n is 2 in general formula (1).

3. A pyrrolidinone derivative or a pharmaceutically acceptable salt thereof or a hydrate of the pharmaceutically acceptable salt as claimed in claim 1, wherein $R^1$ is chlorine, $R_2$ is methyl, and n is 2 in general formula (1).

4. An optically active pyrrolidinone derivative or a pharmaceutically acceptable salt thereof or a hydrate of the pharmaceutically acceptable salt as claimed in claim 1, represented by general formula (2):

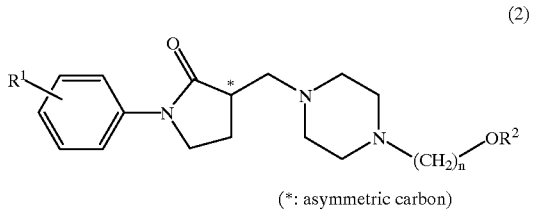

(2)

(*: asymmetric carbon)

wherein $R^1$ is hydrogen or a halogen; $R^2$ is hydrogen, a $C_{1-3}$ alkyl, a $C_{2-3}$ alkenyl or a $C_{2-3}$ alkynyl; and n is an integer of 2 to 3.

5. An optically active pyrrolidinone derivative or a pharmaceutically acceptable salt thereof or a hydrate of the pharmaceutically acceptable salt as claimed in claim 4, wherein $R^1$ is chlorine, $R^2$ is methyl, and n is 2 in general formula (2).

6. The dihydrate of the pharmaceutically acceptable salt of claim 4, wherein $R^1$ is chlorine, $R^2$ is methyl, and n is 2 in general formula (2).

7. An optical resolution method of an optically active pyrrolidinone derivative or a pharmaceutically acceptable salt thereof or a hydrate of the pharmaceutically acceptable salt as claimed in claim 4, comprising;

preparing a mixture of diastereomer salts from a racemic modification of a pyrrolidinone derivative represented by general formula (1),

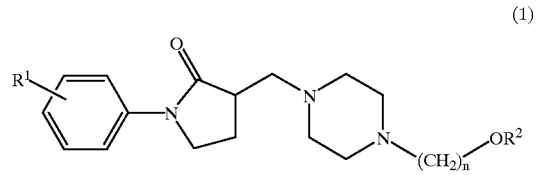

(1)

wherein $R^1$ is hydrogen or a halogen, $R^2$ is hydrogen, a $C_{1-3}$ alkyl, a $C_{2-3}$ alkenyl or a $C_{2-3}$ alkynyl, and n is an integer of 2 to 3, and optically active mandelic acid or optically active tartaric acid;

separating the diastereomer salt of the optically active pyrrolidinone derivative as claimed in claim 4 from the mixture of the diastereomer salts; and forming and collecting the optically active pyrrolidinone derivative as claimed in claim 4 from the separated diastereomer salt.

8. An optical resolution method as claimed in claim 7, wherein $R^1$ is chlorine, $R^2$ is methyl, and n is 2 in general formula (1).

9. An antipsychotic comprising a carrier and the compound as claimed in claim 6 as an active ingredient.

10. An antipsychotic comprising a carrier and the compound as claimed in claim 5 as an active ingredient.

11. An antipsychotic comprising a carrier and the compound as claimed in claim 4 as an active ingredient.

12. An antipsychotic comprising a carrier and the compound as claimed in claim 3 as an active ingredient.

13. An antipsychotic comprising a carrier and the compound as claimed in claim 2 as an active ingredient.

14. An antipsychotic comprising a carrier and the compound as claimed in claim 1 as an active ingredient.

15. An intermediate salt for the preparation of an optically active pyrrolidinone derivative or a pharmaceutically acceptable salt thereof or a hydrate of the pharmaceutically acceptable salt, said intermediate salt consisting of the pyrrolidinone derivative represented by general formula (2) and optically active mandelic acid or optically active tartaric acid:

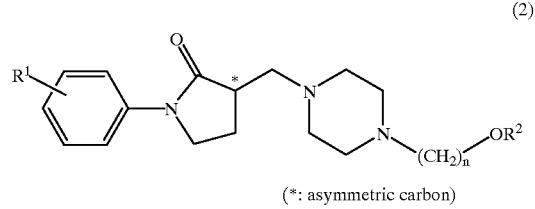

(2)

(*: asymmetric carbon)

wherein $R^1$ is chlorine; $R^2$ is methyl; and n is 2.

* * * * *

UNITED STATES PATENT AND TRADEMARK OFFICE
CERTIFICATE OF CORRECTION

PATENT NO. : 5,969,138
DATED : October 19, 1999
INVENTOR(S) : Naruyoshi Mita et al.

It is certified that error appears in the above-identified patent and that said Letters Patent is hereby corrected as shown below:

Column 1,
Line 39, change "maybe" to -- may be --.

Column 2,
Line 62, change "alkyloxy" to -- alkynyloxy --.

Column 34,
Line 66, change "hydrochloride" to -- dihydrochloride --.

Column 35,
Line 15, change "hydrochloride" to -- dihydrochloride --.
Line 55, change "L-12" to -- m-12 --

Column 36,
Line 23, after "above" delete "r" and insert -- $\sigma_1$ --.

Column 41,
Line 26, change "$R_2$" to -- $R^2$ --.

Signed and Sealed this

Twenty-seventh Day of August, 2002

Attest:

JAMES E. ROGAN
Attesting Officer    Director of the United States Patent and Trademark Office